(12) United States Patent
Umetani et al.

(10) Patent No.: US 7,884,216 B2
(45) Date of Patent: Feb. 8, 2011

(54) FLUORINE-CONTAINING PYRAZOLECARBONITRILE DERIVATIVE AND METHOD FOR PRODUCING THE SAME, AND FLUORINE-CONTAINING PYRAZOLECARBOXYLIC ACID DERIVATIVE OBTAINED BY USING THE FLUORINE-CONTAINING PYRAZOLECARBONITRILE DERIVATIVE AND METHOD FOR PRODUCING THE SAME

(75) Inventors: Hideki Umetani, Ritto (JP); Takeshi Kakimoto, Chiba (JP); Yoji Aoki, Chiba (JP)

(73) Assignee: Mitsui Chemicals Agro, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/527,739

(22) PCT Filed: Feb. 13, 2008

(86) PCT No.: PCT/JP2008/052357

§ 371 (c)(1),
(2), (4) Date: Aug. 19, 2009

(87) PCT Pub. No.: WO2008/102678

PCT Pub. Date: Aug. 28, 2008

(65) Prior Publication Data

US 2010/0016612 A1    Jan. 21, 2010

(30) Foreign Application Priority Data

Feb. 20, 2007    (JP) .............................. 2007-039744

(51) Int. Cl.
*C07D 231/10* (2006.01)
*A61K 31/415* (2006.01)
*A01N 43/56* (2006.01)

(52) U.S. Cl. ................. 548/373.1; 548/356.1; 514/406; 504/280

(58) Field of Classification Search .............. 548/373.1, 548/356.1; 514/406; 504/280
See application file for complete search history.

(56) References Cited

FOREIGN PATENT DOCUMENTS

| | | |
|---|---|---|
| JP | 8-193067 A | 7/1996 |
| JP | 8-208620 A | 8/1996 |
| JP | 2001-342179 A | 12/2001 |
| JP | 2002-128763 A | 5/2002 |
| WO | WO 2005/056015 A1 | 6/2005 |

OTHER PUBLICATIONS

International Search Report (PCT/ISA/210) for PCT/JP2008/052357 completed Mar. 14, 2008.
Written Opinion (PCT/ISA/237) for PCT/JP2008/052357 completed Mar. 14, 2008.
A. Mukherjee et al, On the regiospecificity of 3,5-disubstituted pyrazoles derived from C-acylated-β-enaminonitriles and esters, Indian Journal of Chemistry, Nov. 2005, pp. 2333-2337, vol. 44B.
David E. Tupper et al., "Steric and Electronic Control in the Addition of Hydrazine and Phenylhydrazine to α-[(Dimethylamino)methylene]-β-oxoarylpropanenitriles", Synthesis, Mar. 1997, pp. 337-341, No. 3, England.

*Primary Examiner*—Golam M. M. Shameem
*Assistant Examiner*—Samantha L Shterengarts
(74) *Attorney, Agent, or Firm*—Buchanan Ingersoll & Rooney PC

(57) ABSTRACT

The present invention provides a fluorine-containing pyrazolecarbonitrile derivative and a method for producing the same, and a fluorine-containing pyrazolecarboxylic acid derivative obtained by using the fluorine-containing pyrazolecarbonitrile derivative and a method for producing the same.

A fluorine-containing acyacrylonitrile derivative prepared from a fluoroacyl derivative and an aminoacrylonitrile derivative, is reacted with a hydrazine derivative to produce a fluorine-containing pyrazolecarbonitrile derivative represented by Formula (1).

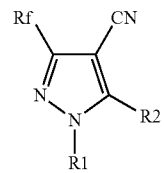

(1)

In Formula (1), Rf represents an alkyl group having 1 to 6 carbon atoms and substituted with at least one fluorine atom; R1 represents an alkyl group having 1 to 6 carbon atoms and R2 represents a hydrogen atom, an alkyl group having 1 to 6 carbon atoms or the like.

The fluorine-containing pyrazolecarbonitrile derivative represented by Formula (1) is reacted with water to produce a fluorine-containing pyrazolecarboxylic acid derivative.

24 Claims, No Drawings

FLUORINE-CONTAINING PYRAZOLECARBONITRILE DERIVATIVE AND METHOD FOR PRODUCING THE SAME, AND FLUORINE-CONTAINING PYRAZOLECARBOXYLIC ACID DERIVATIVE OBTAINED BY USING THE FLUORINE-CONTAINING PYRAZOLECARBONITRILE DERIVATIVE AND METHOD FOR PRODUCING THE SAME

TECHNICAL FIELD

The present invention relates to a fluorine-containing pyrazolecarbonitrile derivative and a method for producing the same, and a fluorine-containing pyrazolecarboxylic acid derivative obtained by using the fluorine-containing pyrazolecarbonitrile derivative and a method for producing the same.

BACKGROUND ART

A group of compounds containing a fluorine-containing pyrazolecarbonitrile derivative is known to be a physiological active substance effective in a field of medicines and agricultural chemicals. Furthermore, a cyano group may be converted into various functional groups such as a carboxylic acid, an aminomethyl group, an aminocarbonyl group, an alkoxyimidoyl group and so on; accordingly, the fluorine-containing pyrazolecarbonitrile derivative may be a useful intermediate for production as well in the field. Accordingly, it is important to provide a novel fluorine-containing pyrazolecarbonitrile derivative and a method for producing the same, and various technical developments have been forwarded.

In what follows, examples of typical preceding technologies will be shown.

(1) A method where a trifluoromethylpyrazole derivative is iodated with [bis(trifluoroacetoxy)iodo]benzene and iodine, followed by introducing a cyano group with copper cyanide (see, for example, Patent literature 1).

(2) A method where a formyl group is introduced in a trifluoromethylpyrazole derivative with a Vilsmeyer reagent, followed by reacting with hydroxylamine, subsequently with phosphorus oxychloride to synthesize a pyrazolecarbonitrile derivative (see, for example, Patent literature 2)

Patent literature 1: WO 05/056015 A1

Patent literature 2: JP-A No. 08-208620

DISCLOSURE OF INVENTION

Problem to be Solved by the Invention

However, regarding the method of (1), reagents such as [bis(trifluoroacetoxy)iodo]benzene, copper cyanide and so on are not preferable from the viewpoint of safeness and transition metals such as copper are problematic from the viewpoint of waste disposal thereof. Furthermore, the number of processes from a trifluoromethyl source is many; accordingly, the method of (1) is not appropriate in an industrial production. The method of (2) as well is problematic. Hydroxylamine that is a reagent problematic from safeness point of view and phosphorus oxychloride that is a reagent problematic from disposal point of view are used and the number of processes is many. Furthermore, a purification process with silica gel column chromatography unfavorable for a mass synthesis is necessary.

The invention intends to provide a novel fluorine-containing pyrazolecarbonitrile derivative and a method for producing the same, which is capable of practicing conveniently and in an industrial scale, and a method for producing a fluorine-containing pyrazolecarboxylic acid derivative obtained by using the fluorine-containing pyrazolecarbonitrile derivative and a novel fluorine-containing pyrazolecarboxylic acid derivative.

Means for Solving Problems

As a result of extensive research in order to solve the above-described problems, it was found that when a 2-fluorine-containing acyl-3-aminoacrylonitrile derivative was prepared from a fluorine-containing acyl derivative and an aminoacrylonitrile derivative, followed by reacting with a hydrazine derivative, an desired fluorine-containing pyrazolecarbonitrile derivative was produced. The method enabled to efficiently provide a novel pyrazolecarbonitrile derivative such as 1-methyl-3-(trifluoromethyl)-1H-pyrazole-4-carbonitrile. Furthermore, it was found that the novel pyrazolecarbonitrile derivative may be efficiently converted into 1-methyl-3-(trifluoromethyl)-1H-pyrazole-4-carboxylic acid that is a very important raw material in agrihorticultural insecticides and so on and thereby may be a very useful production intermediate. Thereby, the invention came to completion.

That is, the invention is as shown below.

1. A fluorine-containing pyrazolecarbonitrile derivative represented by the following Formula (1):

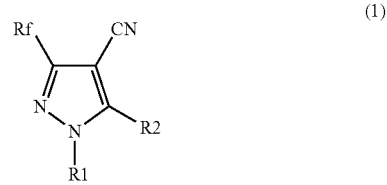

wherein, in Formula (1), Rf represents an alkyl group having 1 to 6 carbon atoms, which is substituted by at least one fluorine atom; R1 represents an alkyl group having 1 to 6 carbon atoms, a cycloalkyl group having 3 to 6 carbon atoms or an arylalkyl group which may be substituted; and R2 represents a hydrogen atom, an alkyl group having 1 to 6 carbon atoms, a cycloalkyl group having 3 to 6 carbon atoms, an aryl group which may be substituted, or an arylalkyl group which may be substituted.

2. The fluorine-containing pyrazolecarbonitrile derivative according to 1, wherein, in Formula (1), R2 represents a hydrogen atom.

3. The fluorine-containing pyrazolecarbonitrile derivative according to 2, wherein, in Formula (1), Rf represents a trifluoromethyl group, a difluoromethyl group, a chlorodifluoromethyl group, a pentafluoroethyl group, or a heptafluoropropyl group; and R1 represents an alkyl group having 1 to 6 carbon atoms.

4. A method for producing a fluorine-containing pyrazolecarboxylic acid derivative represented by the following Formula (2), the method comprising reacting a compound represented by the following Formula (1) with water:

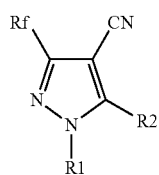

wherein, in Formula (1), Rf represents an alkyl group having 1 to 6 carbon atoms, which is substituted with at least one fluorine atom; R1 represents an alkyl group having 1 to 6 carbon atoms, a cycloalkyl group having 3 to 6 carbon atoms or an arylalkyl group which may be substituted; and R2 represents a hydrogen atom, an alkyl group having 1 to 6 carbon atoms, a cycloalkyl group having 3 to 6 carbon atoms, an aryl group which may be substituted, or an arylalkyl group which may be substituted:

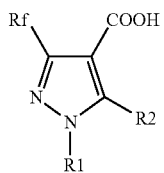

wherein, in Formula (2), Rf, R1 and R2 have the same definition as those described above.

5. The method for producing a fluorine-containing pyrazolecarboxylic acid derivative according to 4, wherein, in compounds represented by Formulae (1) and (2), R2 represents a hydrogen atom.

6. The method for producing a fluorine-containing pyrazolecarboxylic acid derivative according to 5, wherein, in compounds represented by Formulae (1) and (2), R2 represents a trifluoromethyl group, a difluoromethyl group, a chlorodifluoromethyl group, a pentafluoroethyl group, or a heptafluoropropyl group, and R1 represents an alkyl group having 1 to 6 carbon atoms.

7. The method for producing a fluorine-containing pyrazolecarboxylic acid derivative represented by Formula (2) according to 4, which further includes producing a compound represented by Formula (1) according to 4, from a compound represented by the following Formula (3) and a compound represented by the following Formula (4):

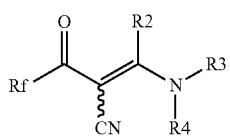

wherein, in Formula (3), Rf and R2 have the same definitions as those described in 4; R3 and R4 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or an atomic group that forms a 5- or 6-membered ring containing 0 or 1 heteroatom with the nitrogen atom to which R3 and R4 are bonded;

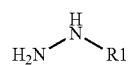

wherein, in Formula (4), R1 has the same definition as that described in 4.

8. The method for producing a fluorine-containing pyrazolecarboxylic acid derivative according to 7, wherein, in compounds represented by Formulae (1), (2), (3) and (4), R2 represents a hydrogen atom; and R3 and R4 each independently represent an alkyl group having 1 to 6 carbon atoms, or a cycloalkyl group having 3 to 6 carbon atoms, or R3 and R4 represent an atomic group that forms a 5- or 6-membered ring containing 0 or 1 heteroatom with the nitrogen atom to which R3 and R4 are bonded.

9. The method for producing a fluorine-containing pyrazolecarboxylic acid derivative according to 8, wherein, in compounds represented by Formulae (1), (2), (3) and (4), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

10. The method for producing a fluorine-containing pyrazolecarboxylic acid derivative according to 8, wherein, in compounds represented by Formulae (1), (2), (3) and (4), Rf represents a difluoromethyl group, a chlorodifluoromethyl group, a pentafluoroethyl group, or a heptafluoropropyl group; R1 represents an alkyl group having 1 to 6 carbon atoms; and R3 and R4 respectively represent a methyl group.

11. The method for producing a fluorine-containing pyrazolecarboxylic acid derivative represented by Formula (2) according to 7, which further includes producing a compound represented by Formula (3) from a compound represented by the following Formula (5) and a compound represented by the following Formula (6):

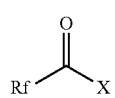

wherein, in Formula (5), Rf has the same definition as that described in 7 and X represents a halogen atom, a hydroxy group, or a carbonyloxy group;

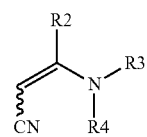

wherein, in Formula (6), R2, R3 and R4 have the same definitions as those described in 7.

12. The method for producing a fluorine-containing pyrazole-carbxylic acid derivative according to 11, wherein, in compounds represented by Formulae (1), (2), (3), (4), (5) and (6), R2 represents a hydrogen atom; R3 and R4 each independently represent an alkyl group having 1 to 6 carbon atoms, or, a cycloalkyl group having 3 to 6 carbon atoms, or an atomic group that forms a 5- or 6-membered ring containing 0 or 1 heteroatom with the nitrogen atom to which R3 and R4 are bonded; and X represents a halogen atom, a hydroxy group or —O(C=O)Rf.

13. The method for producing a fluorine-containing pyrazole-carbxylic acid derivative according to 12, wherein, in compounds represented by Formulae (1), (2), (3), (4), (5) and (6), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

14. The method for producing a fluorine-containing pyrazole-carbxylic acid derivative according to 12, wherein, in compounds represented by Formulae (1), (2), (3), (4), (5) and (6), Rf represents a difluoromethyl group, a chlorodifluoromethyl group, a pentafluoroethyl group, or a heptafluoropropyl group; R1 represents an alkyl group having 1 to 6 carbon atoms; and R3 and R4 respectively represent a methyl group.

15. A method for producing a fluorine-containing pyrazole-carbonitrile derivative represented by the following Formula (1), the method comprising reacting a compound represented by the following Formula (3) with a compound represented by the following Formula (4):

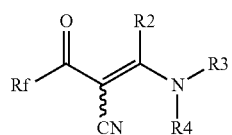

(3)

wherein, in Formula (3), Rf represents an alkyl group having 1 to 6 carbon atoms which is substituted by at least one fluorine atom; and R2 represents a hydrogen atom, an alkyl group having 1 to 6 carbon atoms, a cycloalkyl group having 3 to 6 carbon atoms, an aryl group which may be substituted, or an arylalkyl group which may be substituted; and R3 and R4 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or R3 and R4 represent an atomic group that forms a 5- or 6-membered ring containing 0 or 1 heteroatom with the nitrogen atom to which R3 and R4 are bonded;

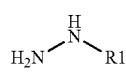

(4)

wherein, in Formula (4), R1 represents an alkyl group having 1 to 6 carbon atoms, a cycloalkyl group having 3 to 6 carbon atoms, or an arylalkyl group which may be substituted;

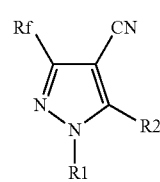

(1)

wherein, in Formula (1), Rf, R1 and R2 have the same definitions as those described above.

16. The method for producing a fluorine-containing pyrazole-carbonitrile derivative according to 15, wherein, in Formulae (1), (3) and (4), R2 represents a hydrogen atom; and R3 and R4 each independently represent an alkyl group having 1 to 6 carbon atoms, or a cycloalkyl group having 3 to 6 carbon atoms, or R3 and R4 represent an atomic group that forms a 5- or 6-membered ring containing 0 or 1 heteroatom with the nitrogen atom to which R3 and R4 are bonded.

17. The method for producing a fluorine-containing pyrazole-carbonitrile derivative according to 16, wherein, in compounds represented by Formulae (1), (3) and (4), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

18. The method for producing a fluorine-containing pyrazole-carbonitrile derivative according to 16, wherein, in compounds represented by Formulae (1), (3) and (4), Rf represents a difluoromethyl group, a chlorodifluoromethyl group, a pentafluoroethyl group, or a heptafluoropropyl group; R1 represents an alkyl group having 1 to 6 carbon atoms; and R3 and R4 respectively represent a methyl group.

19. The method for producing a fluorine-containing pyrazole-carbonitrile derivative represented by Formula (1) according to 15, which further includes producing a compound represented by Formula (3) from a compound represented by the following Formula (5) and a compound represented by represented by the following Formula (6):

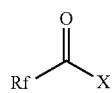

(5)

wherein, in Formula (5), Rf has the same as definition that described in 15; and X represents a halogen atom, a hydroxy group, or a carbonyloxy group;

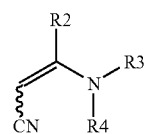

(6)

wherein, in Formula (6), R2, R3 and R4 have the same definitions as those described in 15.

20. The method for producing a fluorine-containing pyrazole-carbonitrile derivative according to 19, wherein, in compounds represented by Formulae (1), (3), (4), (5) and (6), R2 represents a hydrogen atom; R3 and R4 each independently represent an alkyl group having 1 to 6 carbon atoms, or a cycloalkyl group having 3 to 6 carbon atoms, or R3 and R4 represent an atomic group that forms a 5- to 6-membered ring containing 0 or 1 heteroatom with the nitrogen atom to which R3 and R4 are bonded; and X represents a halogen atom, a hydroxy group, or —O(C=O)Rf.

21. The method for producing a fluorine-containing pyrazole-carbonitrile derivative according to 20, wherein, in compounds represented by Formulae (1), (3), (4), (5) and (6), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

22. The method for producing a fluorine-containing pyrazole-carbonitrile derivative according to 20, wherein, in compounds represented by Formulae (1), (3), (4), (5) and (6), Rf represents a difluoromethyl group, a chlorodifluoromethyl group, a pentafluoroethyl group, or a heptafluoropropyl group; R1 represents an alkyl group having 1 to 6 carbon atoms; and R3 and R4 respectively represent a methyl group.

23. A fluorine-containing pyrazolecarboxylic acid derivative represented by the following formula (2):

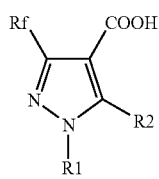

wherein, in Formula (2), Rf represents a perfluoroalkyl group having 2 to 6 carbon atoms; R1 represents an alkyl group having 1 to 6 carbon atoms; and R2 represents a hydrogen atom.

24. The fluorine-containing pyrazolecarboxylic acid derivative according to 23, wherein, in a formula (2), Rf represents a pentafluoroethyl group or a heptafluoropropyl group.

Effects of the Invention

According to the present invention, a novel fluorine-containing pyrazolecarbonitrile derivative, and a method for producing the fluorine-containing pyrazolecarbonitrile derivative, which is capable of practicing conveniently and in an industrial scale, and a method for producing a fluorine-containing pyrazolecarboxylic acid derivative obtained by using the fluorine-containing pyrazolecarbonitrile derivative, and a novel fluorine-containing pyrazolecarboxylic acid derivative may be provided.

BEST MODE FOR CARRYING OUT THE INVENTION

In the following, a best mode for carrying out the present invention will be described in detail.

In the following, a compound represented by the following Formula (1) will be described.

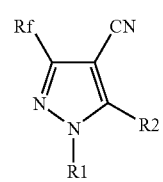

An alkyl group having 1 to 6 carbon atoms in Rf in Formula (1) may be either a straight-chain alkyl group or a branched alkyl group. Examples thereof include straight-chain alkyl groups such as a methyl group, an ethyl group, a propyl group, a butyl group, a pentyl group, or a hexyl group and branched alkyl groups such as an isopropyl group, an isobutyl group, a sec-butyl group, a 1-methylbutyl group, a 2-methylbutyl group, a 3-methylbutyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, or a 3,3-dimethylbutyl group.

Rf in Formula (1) may be any of these alkyl groups having 1 to 6 carbon atoms as long as they are substituted by at least one fluorine atom. Examples thereof include perfluoroalkyl groups such as a trifluoromethyl group, a pentafluoroethyl group, a heptafluoropropyl group, a heptafluoroisopropyl group, or a nonafluorobutyl group, fluoroalkyl groups having a hydrogen atom such as a monofluoromethyl group, or a difluoromethyl group, or fluoroalkyl groups having a fluorine atom and another halogen atom such as a chlorodifluoromethyl group, or a bromodifluoromethyl group.

The Rf in the invention is preferably a fluoroalkyl group selected from a trifluoromethyl group, a difluoromethyl group, a chlorodifluoromethyl group, a pentafluoroethyl group, and a heptafluoropropyl group, a trifluoromethyl group being more preferred.

An alkyl group having 1 to 6 carbon atoms in the R1 in Formula (1) has the same definitions as that of the alkyl group having 1 to 6 carbon atoms in Rf.

Examples of the cycloalkyl group having 3 to 6 carbon atoms in R1 in Formula (1) include a cyclopropyl group, a cyclobutyl group, a cyclopentyl group, a cyclohexyl group and so on.

Examples of the substituent for the arylalkyl group which may be substituted for R1 in Formula (1) include an alkyl group, such as a methyl group, an ethyl group, a propyl group, an isopropyl group, a butyl group, an isobutyl group, a sec-butyl group, or a tert-butyl group; a cycloalkyl group, such as a cyclopropyl group, a cyclobutyl group, a cyclopentyl group, or a cyclohexyl group; a halogen-substituted alkyl group, such as a trifluoromethyl group, a pentafluoroethyl group, a hexafluoropropyl group, a hexafluoroisopropyl group, a trifluoroethyl group, a difluoromethyl group, a chlorodifluoromethyl group, a bromodifluoromethyl group, or a monofluoromethyl group; an aryl group, such as a phenyl group; an arylalkyl group, such as a benzyl group; an alkoxy group, such as a methoxy group, an ethoxy group, a propoxy group, an isopropoxy group, a butoxy group, an isobutoxy group, a sec-butoxy group, or a tert-butoxy group; a cycloalkoxy group, such as a cyclopropoxy group, a cyclobutoxy group, a cyclopentyloxy group, or a cyclohexyloxy group; a halogen-substituted alkoxy group, such as a trifluoromethoxy group, a difluoromethoxy group, a trifluoroethoxy group, or a trichloroethoxy group; an aryloxy group, such as a phenoxy group; an arylalkyloxy group, such as a benzyloxy group; an alkoxycarbonyl group, such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, or a tert-butoxycarbonyl group; a cycloalkoxycarbonyl group, such as a cyclopropoxycarbonyl group, a cyclobutoxycarbonyl group, a cyclopentyloxycarbonyl group, or a cyclohexyloxycarbonyl group; a halogen-substituted alkoxycarbonyl group, such as a trifluoromethoxycarbonyl group, a difluoromethoxycarbonyl group, a trifluoroethoxycarbonyl group, or a trichloroethoxycarbonyl group; an aryloxycarbonyl group, such as a phenoxycarbonyl group; an arylalkyloxycarbonyl group, such as benzyloxycarbonyl group; an alkylthio group, such as a methylthio group, an ethylthio group, a propylthio group, or a butylthio group; a cycloalkylthio group, such as a cyclopropylthio group, a cyclobutylthio group, a cyclopentylthio group, or a cyclohexylthio group; a halogen-substituted alkylthio group such as a trifluoromethylthio group, a difluoromethylthio group, or a trifluoroethylthio group; an arylthio group, such as a phenylthio group; an arylalkylthio group, such as a benzylthio group; an alkylsulfinyl group, such as a methanesulfinyl group, an ethanesulfinyl group, a propanesulfinyl group, or a butanesulfinyl group; a cycloalkylsulfinyl group, such as a cyclopropanesulfinyl group, a cyclobutanesulfinyl group, a cyclopentanesulfinyl group, or a cyclohexanesulfinyl group; a halogen-substituted alkylsulfinyl group, such as a trifluoromethanesulfinyl group, a difluoromethanesulfinyl group, or a trifluoroethanesulfinyl group; an arylsulfinyl group, such as a phenylsulfinyl group; an aryalkylsulfinyl group, such as a benzylsulfinyl group; an alkylsulfonyl group, such as a methanesulfonyl group, an ethanesulfonyl group, a propanesulfonyl group, or a butanesulfonyl group; a cycloalkylsulfonyl group, such as a cyclopropanesulfonyl group, a cyclobutanesulfonyl group, a cyclopentanesulfonyl group, or a cyclohexanesulfonyl group; a halogen-substituted alkylsulfonyl group, such as a trifluoromethanesulfonyl group, a difluoromethanesulfonyl group, or a trifluoroethanesulfonyl group; an arylsulfonyl group, such as a phenylsulfonyl group; an arylalkylsulfonyl group, such as a benzylsulfonyl group; an alkylcarbonyl group, such as a methylcarbonyl group, an ethylcarbonyl group, a propylcarbonyl group, an isopropylcarbonyl group, a butylcarbonyl group, an isobutylcarbonyl group, a sec-butylcarbonyl group, or a tert-butylcarbonyl group; a cycloalkylcarbonyl group, such as a cyclopropylcarbonyl group, a cyclobutylcarbonyl group, a cyclopropylcarbonyl group, a cyclopentylcarbonyl group, or a cyclohexylcarbonyl group; a halogen-substituted alkylcarbonyl group, such as a trifluoromethanecarbonyl group, a difluoromethanecarbonyl group, or a trichloromethanecarbonyl group; an arylcarbonyl group, such as a benzoyl group; an alkylcarbonyloxy group, such as a methylcarbonyloxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, or a tert-butylcarbonyloxy group; a cycloalkylcarbonyloxy group, such as a cyclopropylcarbonyloxy group, a cyclobutylcarbonyloxy group, a cyclopropylcarbonyloxy group, a cyclopentylcarbonyloxy group, or a cyclohexylcarbonyloxy group; an arylcarbonyloxy group, such as a benzoyloxy group; an alkylcarbonylamino group, such as a methylcarbonylamino group, an ethylcarbonylamino group, a propylcarbonylamino group, an isopropylcarbonylamino group, a butylcarbonylamino group, an isobutylcarbonylamino group, a sec-butylcarbonylamino group, or a tert-butylcarbonylamino group; a cycloalkylcarbonylamino group, such as a cyclopropylcarbonylamino group, a cyclobutylcarbonylamino group, a cyclopropylcarbonylamino group, a cyclopentylcarbonylamio group or a cyclohexylcarbonylamino group; an arylcarbonylamino group, such as a benzoylamino group; an alkoxycarbonylamino group, such as a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a methoxycarbonyl(methyl)amino group, an ethoxycarbonyl(methyl)amino group, a propoxycarbonyl(methyl)amino group, an isopropoxycarbonyl(methyl)amino group, a butoxycarbonyl(methyl)amino group, an isobutoxycarbonyl(methyl)amino group, a sec-butoxycarbonyl(methyl)amino group, a tert-butoxycarbonyl(methyl)amino group, a methoxycarbonyl(ethyl)amino group, an ethoxycarbonyl(ethyl)amino group, a propoxycarbonyl(ethyl)amino group, an isopropoxycarbonyl(ethyl)amino group, a butoxycarbonyl(ethyl)amino group, an isobutoxycarbonyl(ethyl)amino group, a sec-butoxycarbonyl(ethyl)amino group, or a tert-butoxycarbonyl(ethyl)amino group; cycloalkoxycarbonylamino groups such as a cyclopropoxycarbonylamino group, a cyclobutoxycarbonylamino group, a cyclopentyloxycarbonylamino group, a cyclohexyloxycarbonylamino group, a cyclopropoxycarbonyl(methyl)amino group, a cyclobutoxycarbonyl(methyl)amino group, a cyclopentyloxycarbonyl(methyl)amino group, a cyclohexyloxycarbonyl(methyl)amino group, a cyclopropoxycarbonyl(ethyl)amino group, a cyclobutoxycarbonyl(ethyl)amino group, a cyclopentyloxycarbonyl(ethyl)amino group, or a cyclohexyloxycarbonyl(ethyl)amino group; a halogen-substituted alkoxycarbonylamino group, such as a trifluoromethoxycarbonylamino group, a difluoromethoxycarbonylamino group, a trifluoroethoxycarbonylamino group, a trichloroethoxycarbonylamino group, a trifluoromethoxycarbonyl(methyl)amino group, a difluoromethoxycarbonyl(methyl)amino group, a trifluoroethoxycarbonyl(methyl)amino group, a trichloroethoxycarbonyl(methyl)amino group, a trifluoromethoxycarbonyl(ethyl)amino group, a difluoromethoxycarbonyl(ethyl)amino group, a trifluoroethoxycarbonyl(ethyl)amino group, or a trichloroethoxycarbonyl(ethyl)amino group; an aryloxycarbonylamino group, such as a phenoxycarbonylamino group, a phenoxycarbonyl(methyl)amino group, or a phenoxycarbonyl(ethyl)amino group; an arylalkyloxycarbonylamino group, such as a benzyloxycarbonylamino group, a benzyloxycarbonyl(methyl)amino group or a benzyloxycarbonyl(ethyl)amino group; an alkylaminocarbonyloxy group, such as a methylaminocarbonyloxy group, an ethylaminocarbonyloxy group, a propylaminocarbonyloxy group, an isopropylaminocarbonyloxy group, a butylaminocarbonyloxy group, an isobutylaminocarbonyloxy group, a sec-butylaminocarbonyloxy group, a tert-butylaminocarbonyloxy group, a dimethylaminocarbonyloxy group, an {ethyl(methyl)amino}carbonyloxy group, a {propyl(methyl)amino}carbonyloxy group, an {isopropyl(methyl)amino}carbonyloxy group, a {butyl(methyl)amino}carbonyloxy group, an {isobutyl(methyl)amino}carbonyloxy group, a {sec-butyl(methyl)amino}carbonyloxy group, a {tert-butyl(methyl)amino}carbonyloxy group, a diethylaminocarbonyloxy group, a {propyl(ethyl)amino}carbonyloxy group, an {isopropyl(ethyl)amino}carbonyloxy group, a {butyl(ethyl)amino}carbonyloxy group, an {isobutyl(ethyl)amino}carbonyloxy group, a {sec-butyl(ethyl)amino}carbonyloxy group, or a {tert-butyl(ethyl)

amino}carbonyloxy group; a cycloalkylaminocarbonyloxy group, such as a cyclopropylaminocarbonyloxy group, a cyclobutylaminocarbonyloxy group, a cyclopentylaminocarbonyloxy group, a cyclohexylaminocarbonyloxy group, a {cyclopropyl(methyl)amino}carbonyloxy group, a {cyclobutyl(methyl)amino}carbonyloxy group, a {cyclopentyl(methyl)amino}carbonyloxy group, a {cyclohexyl(methyl)amino}carbonyloxy group, a {cyclopropyl(ethyl)amino}carbonyloxy group, a {cyclobutyl(ethyl)amino}carbonyloxy group, a {cyclopentyl(ethyl)amino}carbonyloxy group, or a {cyclohexyl(ethyl)amino}carbonyloxy group; a halogen-substituted alkylaminocarbonyloxy group, such as a trifluoromethylaminocarbonyloxy group, a difluoromethylaminocarbonyloxy group, a trifluoroethylaminocarbonyloxy group, a trichloroethylaminocarbonyloxy group, a {trifluoromethyl(methyl)amino}carbonyloxy group, a {difluoromethyl(methyl)amino}carbonyloxy group, a {trifluoroethyl(methyl)amino}carbonyloxy group, a {trichloroethyl(methyl)amino}carbonyloxy group, a {trifluoromethyl(ethyl)amino}carbonyloxy group, a {difluoromethyl(ethyl)amino}carbonyloxy group, a {trifluoroethyl(ethyl)amino}carbonyloxy group, or a {trichloroethyl(ethyl)amino}carbonyloxy group; an arylaminocarbonyloxy group, such as a phenylaminocarbonyloxy group, a {phenyl(methyl)amino}carbonyloxy group or a {phenyl(ethyl)amino}carbonyloxy group; an arylalkylaminocarbonyloxy group, such as a benzylaminocarbonyloxy group, a {benzyl(methyl)amino}carbonyloxy group, or a {benzyl(ethyl)amino}carbonyloxy group; a cyclic aminocarbonyloxy group, such as a pyrrolidinocarbonyloxy group, a piperidinocarbonyloxy group or a morpholinocarbonyloxy group; an alkylaminocarbonylamino group, such as a methylaminocarbonylamino group, an ethylaminocarbonylamino group, a propylaminocarbonylamino group, an isopropylaminocarbonylamino group, a butylaminocarbonylamino group, an isobutylaminocarbonylamino group, a sec-butylaminocarbonylamino group, a tert-butylaminocarbonylamino group, a dimethylaminocarbonylamino group, an {ethyl(methyl)amino}carbonylamino group, a {propyl(methyl)amino}carbonylamino group, an {isopropyl(methyl)amino}carbonylmethyl group, a {butyl(methyl)amino}carbonylamino group, an {isobutyl(methyl)amino}carbonylamino group, a {sec-butyl(methyl)amino}carbonylamino group, a {tert-butyl(methyl)amino}carbonylamino group, a diethylaminocarbonylamino group, a {propyl(ethyl)amino}carbonylamino group, an {isopropyl(ethyl)amino}carbonylamino group, a {butyl(ethyl)amino}carbonylamino group, an {isobutyl(ethyl)amino}carbonylamino group, a {sec-butyl(ethyl)amino}carbonylamino group, a {tert-butyl(ethyl)amino}carbonylamino group, a methylaminocarbonyl(methyl)amino group, an ethylaminocarbonyl(methyl)amino group, a propylaminocarbonyl(methyl)amino group, an isopropylaminocarbonyl(methyl)amino group, a butylaminocarbonyl(methyl)amino group, an isobutylaminocarbonyl(methyl)amino group, a sec-butylaminocarbonyl(methyl)amino group, a tert-butylaminocarbonyl(methyl)amino group, a methylaminocarbonyl(ethyl)amino group, an ethylaminocarbonyl(ethyl)amino group, a propylaminocarbonyl(ethyl)amino group, an isopropylaminocarbonyl(ethyl)amino group, a butylaminocarbonyl(ethyl)amino group, an isobutylaminocarbonyl(ethyl)amino group, a sec-butylaminocarbonyl(ethyl)amino group, a tert-butylaminocarbonyl(ethyl)amino group, a dimethylaminocarbonyl(methyl)amino group, an {ethyl(methyl)amino}carbonyl(methyl)amino group, a {propyl(methyl)amino}carbonyl(methyl)amino group, an {isopropyl(methyl)amino}carbonyl(methyl)amino group, a {butyl(methyl)amino}carbonyl(methyl)amino group, an {isobutyl(methyl)amino}carbonyl(methyl)amino group, a {sec-butyl(methyl)amino}carbonyl(methyl)amino group, a {tert-butyl(methyl)amino}carbonyl(methyl)amino group, a dimethylaminocarbonyl(ethyl)amino group, an {ethyl(methyl)amino}carbonyl(ethyl)amino group, a {propyl(methyl)amino}carbonyl(ethyl)amino group, an {isopropyl(methyl)amino}carbonyl(ethyl)amino group, a {butyl(methyl)amino}carbonyl(ethyl)amino group, an {isobutyl(methyl)amino}carbonyl(ethyl)amino group, a {sec-butyl(methyl)amino}carbonyl(ethyl)amino group, a {tert-butyl(methyl)amino}carbonyl(ethyl)amino group, a diethylaminocarbonyl(methyl)amino group, an {ethyl(propyl)amino}carbonyl(methyl)amino group, an {ethyl(isopropyl)amino}carbonyl(methyl)amino group, a {butyl(ethyl)amino}carbonyl(methyl)amino group, an {ethyl(isobutyl)amino}carbonyl(methyl)amino group, a {sec-butyl(ethyl)amino}carbonyl(methyl)amino group, a {tert-butyl(ethyl)amino}carbonyl(methyl)amino group, a diethylaminocarbonyl(ethyl)amino group, an {ethyl(propyl)amino}carbonyl(ethyl)amino group, an {ethyl(isopropyl)amino}carbonyl(ethyl)amino group, an {ethyl(butyl)amino}carbonyl(ethyl)amino group, an {ethyl(isobutyl)amino}carbonyl(ethyl)amino group, a {sec-butyl(ethyl)amino}carbonyl(ethyl)amino group, or a {tert-butyl(ethyl)amino}carbonyl(ethyl)amino group; a cycloalkylaminocarbonylamino group, such as a cyclopropylaminocarbonylamino group, a cyclobutylaminocarbonylamino group, a cyclopentylaminocarbonylamino group, a cyclohexylaminocarbonylamino group, a {cyclopropyl(methyl)amino}carbonylamino group, a {cyclobutyl(methyl)amino}carbonylamino group, a {cyclopentyl(methyl)amino}carbonylamino group, a {cyclohexyl(methyl)amino}carbonylamino group, a {cyclopropyl(ethyl)amino}carbonylamino group, a {cyclobutyl(ethyl)amino}carbonylamino group, a {cyclopentyl(ethyl)amino}carbonylamino group, a {cyclohexyl(ethyl)amino}carbonylamino group, a cyclopropylaminocarbonyl(methyl)amino group, a cyclobutylaminocarbonyl(methyl)amino group, a cyclopentylaminocarbonyl(methyl)amino group, a cyclohexylaminocarbonyl(methyl)amino group, a cyclopropylaminocarbonyl(ethyl)amino group, a cyclobutylaminocarbonyl(ethyl)amino group, a cyclopentylaminocarbonyl(ethyl)amino group, a cyclohexylaminocarbonyl(ethyl)amino group, a {cyclopropyl(methyl)amino}carbonyl(methyl)amino group, a {cyclobutyl(methyl)amino}carbonyl(methyl)amino group, a {cyclopentyl(methyl)amino}carbonyl(methyl)amino group, a {cyclohexyl(methyl)amino}carbonyl(methyl)amino group, a {cyclopropyl(methyl)amino}carbonyl(ethyl)amino group, a {cyclobutyl(methyl)amino}carbonyl(ethyl)amino group, a {cyclopentyl(methyl)amino}carbonyl(ethyl)amino group, a {cyclohexyl(methyl)amino}carbonyl(ethyl)amino group, a {cyclopropyl(ethyl)amino}carbonyl(methyl)amino group, a {cyclobutyl(ethyl)amino}carbonyl(methyl)amino group, a {cyclopentyl(ethyl)amino}carbonyl(methyl)amino group, a {cyclohexyl(ethyl)amino}carbonyl(methyl)amino group, a {cyclopropyl(ethyl)amino}carbonyl(ethyl)amino group, a {cyclobutyl(ethyl)amino}carbonyl(ethyl)amino group, a {cyclopentyl(ethyl)amino}carbonyl(ethyl)amino group, or a {cyclohexyl(ethyl)amino}carbonyl(ethyl)amino group; a halogen-substituted alkylaminocarbonylamino group, such as a trifluoromethylaminocarbonylamino group, a difluoromethylaminocarbonylamino group, a trifluoroethylaminocarbonylamino group, a trichloroethylaminocarbonylamino group, a {trifluoromethyl(methyl)amino}carbonylamino group, a {difluoromethyl(methyl)amino}carbonylamino group, a {trifluoroethyl(methyl)amino}carbonylamino group, a {trichloroethyl(methyl)amino}carbonylamino group, a {trifluoromethyl(ethyl)amino}carbonylamino group, a {difluoromethyl(ethyl)amino}carbonylamino group, a {trifluoroethyl(ethyl)amino}carbonylamino group, a {trichloroethyl(ethyl)amino}carbonylamino group, a trifluoromethylaminocarbonyl(methyl)amino group, a difluoromethylaminocarbonyl(methyl)amino group, a trifluoroethylaminocarbonyl(methyl)amino group, a trichloroethylaminocarbonyl(methyl)amino group, a trifluoromethylaminocarbonyl(ethyl)amino group, a difluoromethylaminocarbonyl(ethyl)amino group, a trifluoroethylaminocarbonyl(ethyl)amino group, a trichloroethylaminocarbonyl(ethyl)amino group, a {trifluoromethyl(methyl)amino}carbonyl(methyl)amino group, a {difluoromethyl(methyl)amino}carbonyl(methyl)amino group, a {trifluoroethyl(methyl)amino}carbonyl(methyl)amino group, a {trichloroethyl(methyl)amino}carbonyl(methyl)amino group, a {trifluoromethyl(methyl)amino}carbonyl(ethyl)amino group, a {difluoromethyl(methyl)amino}carbonyl(ethyl)amino group, a {trifluoroethyl(methyl)amino}carbonyl(ethyl)amino group, a {trichloroethyl(methyl)amino}carbonyl(ethyl)amino group, a {trifluoromethyl(ethyl)amino}carbonyl(methyl)amino group, a {difluoromethyl(ethyl)amino}carbonyl(methyl)amino group, a {trifluoroethyl(ethyl)amino}carbonyl(methyl)amino group, a {trichloroethyl(ethyl)amino}carbonyl(methyl)amino group, a {trifluoromethyl(ethyl)amino}carbonyl(ethyl)amino group, a {difluoromethyl(ethyl)amino}carbonyl(ethyl)amino group, a {trifluoroethyl(ethyl)amino}carbonyl(ethyl)amino group, or a {trichloroethyl(ethyl)amino}carbonyl(ethyl)amino group; an arylaminocarbonylamino group, such as a phenylaminocarbonylamino group, a {phenyl(methyl)amino}carbonylamino group, a {phenyl(ethyl)amino}carbonylamino group, a phenylaminocarbonyl(methyl)amino group, a phenylaminocarbonyl(ethyl)amino group, a {methyl(phenyl)amino}carbonyl(methyl)amino group, a {methyl(phenyl)amino}carbonyl(ethyl)amino group, an {ethyl(phenyl)amino}carbonyl(methyl)amino group, or an {ethyl(phenyl)amino}carbonyl(ethyl)amino group; an arylalkylaminocarbonylamino group, such as a benzylaminocarbonylamino group, a {benzyl(methyl)amino}carbonylamino group, a {benzyl(ethyl)amino}carbonylamino group, a benzylaminocarbonyl(methyl)amino group, a benzylaminocarbonyl(ethyl)amino group, a {methyl(benzyl)amino}carbonyl(methyl)amino group, a {methyl(benzyl)amino}carbonyl(ethyl)amino group, an {ethyl(benzyl)amino}carbonyl(methyl)amino group, or an {ethyl(benzyl)amino}carbonyl(ethyl)amino group; a cyclic aminocarbonylamino group, such as a pyrrolidinocarbonylamino group, a piperidinocarbonylamino group, a morpholinocarbonylamino group, a pyrrolidinocarbonyl(methyl)amino group, a piperidinocarbonyl(methyl)amino group, a morpholinocarbonyl(methyl)amino group, a pyrrolidinocarbonyl(ethyl)amino group, a piperidinocarbonyl(ethyl)amino group, or a morpholinocarbonyl(ethyl)amino group; an alkylaminocarbonyl group, such as a methylaminocarbonyl group, an ethylaminocarbonyl group, a propylaminocarbonyl group, an isopropylaminocarbonyl group, a butylaminocarbonyl group, an isobutylaminocarbonyl group, a sec-butylaminocarbonyl group, a tert-butylaminocarbonyl group, a dimethylaminocarbonyl group, an {ethyl(methyl)amino}carbonyl group, a {methyl(propyl)amino}carbonyl group, an {isopropyl(methyl)amino}carbonyl group, a {butyl(methyl)amino}carbonyl group, an {isobutyl(methyl)amino}carbonyl group, a {sec-butyl(methyl)amino}carbonyl group, a {tert-butyl(methyl)amino}carbonyl group, an {ethyl(methyl)amino}carbonyl group, an {ethyl(propyl)amino}carbonyl group, an {ethyl(isopropyl)amino}carbonyl group, a {butyl(ethyl)amino}carbonyl group, an {isobutyl(ethyl)amino}carbonyl group, a {sec-butyl(ethyl)amino}carbonyl group, or a {tert-butyl(ethyl)amino}carbonyl group; a cycloalkylaminocarbonyl group, such as a cyclopropylaminocarbonyl group, a cyclobutylaminocarbonyl group, a cyclopentylaminocarbonyl group, a cyclohexylaminocarbonyl group, a {cyclopropyl(methyl)amino}carbonyl group, a {cyclobutyl(methyl)amino}carbonyl group, a {cyclopentyl(methyl)amino}carbonyl group, a {cyclohexyl(methyl)amino}carbonyl group, a {cyclopropyl(ethyl)amino}carbonyl group, a {cyclobutyl(ethyl)amino}carbonyl group, a {cyclopentyl(ethyl)amino}carbonyl group, or a {cyclohexyl(ethyl)amino}carbonyl group; a halogen-substituted alkylaminocarbonyl group, such as a trifluoromethylaminocarbonyl group, a difluoromethylaminocarbonyl group, a trifluoroethylaminocarbonyl group, a trichloroethylaminocarbonyl group, a {trifluoromethyl(methyl)amino}carbonyl group, a {difluoromethyl(methyl)amino}carbonyl group, a {trifluoroethyl(methyl)amino}carbonyl group, a {trichloroethyl(methyl)amino}carbonyl group, a {trifluoromethyl(ethyl)amino}carbonyl group, a {difluoromethyl(ethyl)amino}carbonyl group, a {trifluoroethyl(ethyl)amino}carbonyl group, or a {trichloroethyl(ethyl)amino}carbonyl group; an arylaminocarbonyl group, such as a phenylaminocarbonyl group, a {phenyl(methyl)amino}carbonyl group, or a {phenyl(ethyl)amino}carbonyl group; an arylalkylaminocarbonyl group, such as a benzylaminocarbonyl group, a {benzyl(methyl)amino}carbonyl group or a {benzyl(ethyl)amino}carbonyl group; a cyclic aminocarbonyl group, such as a pyrrolidinocarbonyl group, a piperidinocarbonyl group or a morpholinocarbonyl group; an alkoxycarbonyloxy group, such as a methoxycarbonyloxy group, an ethoxycarbonyloxy group, a propoxycarbonyloxy group, an isopropoxycarbonyloxy group, a butoxycarbonyloxy group, an isobutoxycarbonyloxy group, a sec-butoxycarbonyloxy group, or a tert-butoxycarbonyloxy group; a cycloalkoxycarbonyloxy group, such as a cyclopropoxycarbonyloxy group, a cyclobutoxycarbonyloxy group, a cyclopentyloxycarbonyloxy group, or a cyclohexyloxycarbonyloxy group; a halogen-substituted alkoxycarbonyloxy group, such as a trifluoromethoxycarbonyloxy group, a difluoromethoxycarbonyloxy group, a trifluoroethoxycarbonyloxy group or a trichloroethoxycarbonyloxy group; an aryloxycarbonyloxy group, such as a phenoxycarbonyloxy group; an arylalkyloxycarbonyloxy group, such as a benzyloxycarbonyloxy group; an alkylamino group, such as a methylamino group, an ethylamino group, a propylamino group, an isopropylamino group, a dimethylamino group, a diethylamino group, a dipropylamino group, or a diisopropylamino group; a cyclic amino group, such as a pyrrolidino group, a piperidino group, or a morpholino group; a silyloxy group, such as a tert-butyldimethylsilyloxy group, a tert-butyldiphenylsilyloxy group or a dimethylphenylsilyloxy group; a halogen atom, such as chlorine, fluorine, bromine or iodine; a nitro group; and a cyano group.

A substitution position of the substituent may be on the aryl moiety that constitutes the arylalkyl group or on the alkyl moiety, and preferably on an aryl moiety. The number of substituents on the arylalkyl group is not restricted. When the arylalkyl group is substituted at two or more positions, the substituents may be the same or composed of two or more kinds, without particularly being limited.

The aryl group of the arylalkyl group which may be substituted for R1 in Formula (1) represents a phenyl group, a naphthyl group, an anthracenyl group or a phenanthrenyl group.

The alkyl moiety of the substitutable arylalkyl group for R1 in Formula (1) represents an alkylene group having 1 to 4 carbon atoms.

The alkyl group having 1 to 6 carbon atoms for R2 in Formula (1) has the same definition as the allyl group having 1 to 6 carbon atoms for Rf.

The cycloalkyl group having 3 to 6 carbon atoms for R2 in Formula (1) has the same definition as the cycloalkyl group having 3 to 6 carbon atoms for R1.

The substituent in the aryl group which may be substituted for R2 in Formula (1) has the same definition as the substituent in the arylalkyl group which may be substituted for R1.

The aryl group in the aryl group which may be substituted for R2 in Formula (1) has the same definition as the aryl group in the arylalkyl group which may be substituted for R1.

The arylalkyl group which may be substituted for R2 in Formula (1) has the same definition as the arylalkyl group which may be substituted for R1.

As the fluorine-containing pyrazolecarbonitrile derivative represented by Formula (1) in the present invention, a compound where R2 is a hydrogen atom is preferred, a compound where R2 is a hydrogen atom, and Rf is an alkyl group having 1 to 3 carbon atoms that is substituted by at least one fluorine atom is more preferred, a compound where R2 is a hydrogen atom, Rf is a trifluoromethyl group, a difluoromethyl group, a chlorodifluoromethyl group, a pentafluoroethyl group, or a heptafluoropropyl group, and R1 is an alkyl group having 1 to 6 carbon atoms is still more preferred, and a compound where R2 is a hydrogen atom, Rf is a trifluoromethyl group, and R1 is an alkyl group having 1 to 6 carbon atoms is furthermore preferred.

In the following, compounds represented by Formula (2) below will be described.

[Kagaku 15]

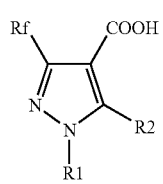

(2)

Rf in Formula (2) has the same definition as the Rf in Formula (1).

R1 in Formula (2) has the same definition as the R1 in Formula (1).

R2 in Formula (2) has the same definition as the R2 in Formula (1).

The method for producing a fluorine-containing pyrazolecarboxylic acid derivative represented by Formula (2) in the present invention includes a process where a compound represented by Formula (1) reacts with water. When the method for producing is thus configured, a fluorine-containing pyrazolecarboxylic acid derivative represented by Formula (2) may be produced conveniently and with a high yield.

Furthermore, the method for producing a fluorine-containing pyrazolecarboxylic acid derivative represented by Formula (2) in the invention may further include, as required, processes for producing, post-processing and purifying a fluorine-containing pyrazolecarbonitrile derivative represented by Formula (1).

In the following, a hydrolysis reaction where the compound represented by Formula (1) reacts with water and converted into the compound represented by Formula (2) will be described.

In order to forward a hydrolysis reaction, it is preferable to use an acid or a base.

In the beginning, a hydrolysis reaction where the compound represented by Formula (1) reacts with water under an acidic condition and is converted into the compound represented by Formula (2) will be described.

A usage amount of water is not particularly limited insofar as it is two equivalents or more to the compound represented by Formula (1). Furthermore, water may be used as a solvent as well. A usage amount as a solvent is not particularly limited insofar as it satisfies the number of the equivalents. Usually, the upper limit thereof may be set at a weight 40 times or less a weight of the compound represented by Formula (1).

An acid to be used may be an organic acid or an inorganic acid insofar as the reaction may proceed.

Examples of organic acid include sulfonates such as methane sulfonate or toluene sulfonate and carboxylic acids such as trichloroacetic acid or trifluoroacetic acid.

Examples of inorganic acid include hydrochloric acid, hydrobromic acid, and sulfuric acid.

A usage amount of the acid is not particularly limited insofar as the desired reaction may proceed. Usually, 0.1 equivalent or more to the compound represented by Formula (1) may be sufficient.

In the present invention, a solvent may be used. Examples of solvent used include carboxylic acid solvent such as acetic acid, alcoholic solvents such as methanol, ethanol, propanol, isopropyl alcohol, or butanol, ether solvents such as tetrahydrofuran, or dioxane, and water. These solvents may be used singularly or in a combination of at least two kinds thereof at an arbitrary mixing ratio.

A usage amount of solvent is not particularly limited. Usually, 3 or more times and 40 or less times a weight of the compound represented by Formula (1) are preferred.

A reaction temperature is not particularly limited insofar as the desired reaction may proceed. The reaction temperature is usually set at 0° C. or more and 150° C. or less, or at a boiling temperature of the solvent or less.

As to a method of post-processing of the reaction mixture containing the compound represented by Formula (2), which is obtained by reacting the compound represented by Formula (1) with water under an acidic condition, there is no particular limitation, insofar as the compound that is represented by Formula (2) and the desired product is not decomposed. In the following, a specific example of the method of post-processing will be described.

When the compound represented by Formula (2) is precipitated from the reaction mixture or the reaction mixture from which the solvent is distilled off, the precipitate may be collected by filtration.

The reaction mixture or the reaction mixture from which the solvent is distilled off may be subjected to liquid separation. At this time, as required, water or an organic solvent may be added. Water used in the liquid separation may contain a salt such as sodium chloride. Furthermore, the number of times of the liquid separation is not limited.

The organic solvent used in the liquid separation is not particularly limited insofar as the compound represented by Formula (2) is not decomposed.

Examples of the organic solvent include halogen solvents, such as dichloromethane, chloroform, or 1,2-dichloroethane, aromatic solvents, such as benzene, toluene, xylene or anisole, ether solvents, such as diethyl ether, or diisopropyl ether, hydrocarbon solvents, such as heptane, hexane, or cyclohexane, and ester solvents, such as ethyl acetate, isopropyl acetate, or butyl acetate. The solvents may be used singularly or in a combination of at lest two kinds thereof at an arbitrary mixing ratio.

The amount of the organic solvent is not limited. Usually, 1 times or more and 40 times or less a weight of the compound represented by Formula (2) are preferred.

The organic layer containing the compound represented by Formula (2) that is obtained by liquid separation may be dewatered with sodium sulfate or magnesium sulfate.

When the organic layer containing the compound represented by Formula (2) that is obtained by liquid separation or the organic layer that is dewatered with sodium sulfate or magnesium sulfate is concentrated under reduced pressure to remove the solvent, the compound is obtained. Furthermore, according to a desired level of purity, the resulted compound may be recrystallized, reprecipitated, washed with a solvent or distilled to purify.

The solvent used when recrystallization, reprecipitation or solvent washing is conducted is not particularly limited insofar as the compound represented by Formula (2) is not decomposed.

Specific examples of the solvent that is used in the recrystallization, reprecipitation and solvent washing include halogen solvents, such as dichloromethane, chloroform, or 1,2-dichloroethane, aromatic solvents, such as benzene, toluene, xylene or anisole, ether solvents, such as diethyl ether, diisopropyl ether, 1,2-dimethoxyethane, tetrahydrofuran, or dioxane, alcohol solvents, such as methanol, ethanol, or isopropyl alcohol, hydrocarbon solvents, such as heptane, hexane, or cyclohexane, ester solvents, such as ethyl acetate, isopropyl acetate, or butyl acetate, nitrile solvents, such as acetonitrile, or propionitrile, and water. The solvents may be used singularly or in a combination of at least two kinds thereof at an arbitrary mixing ratio.

The amount of the solvent may be set according to a desired level of yield and purity without limitation. Usually, the amount of the solvent is a weight preferably 1 times or more and 40 times or less a weight of the compound represented by Formula (2).

In the next place, a hydrolysis reaction where the compound represented by Formula (1) reacts with water under a basic condition to convert into the compound represented by Formula (2) will be described.

The amount of water is not particularly limited, insofar as it is two equivalents or more to the compound represented by Formula (1). At this time, water may be used as a solvent as well. The amount as the solvent is not particularly limited, insofar as it satisfies the number of the equivalents. Usually, the upper limit thereof may be set at a weight 40 times or less a weight of the compound represented by Formula (1).

The base to be used may be an organic base or an inorganic base without particular limitation, insofar as the reaction may proceed.

Specific examples of the organic base include metal alkoxides, such as sodium methoxide or sodium ethoxide, secondary amines, such as diisopropylamine, tertiary amines, such as triethylamine, tributylamine, trioctylamine, diisopropylethylamine, 1,4-diazabicyclo[2.2.2]octane, or 1,8-diazabicyclo[5.4.0]-7-undecene, and aromatic amines, such as pyridine, collidine, lutidine, or 4-dimethylaminopyridine.

Specific examples of the inorganic base include lithium hydroxide, sodium hydroxide, potassium hydroxide, sodium hydrogen carbonate, potassium hydrogen carbonate, sodium carbonate, and potassium carbonate.

The bases may be used singularly or in a combination of at least two kinds thereof in an arbitrary mixing ratio.

The amount of the base is not particularly limited, insofar as the desired reaction may be forwarded. Usually, 0.1 equivalent or more and 20 equivalents or less to the compound represented by Formula (1) may be sufficient.

A solvent may be used in the reaction. Examples of the solvent to be used include alcoholic solvents, such as methanol, ethanol, propanol, isopropyl alcohol or butanol, ether solvents, such as tetrahydrofuran or dioxane, and water. These solvents may be used singularly or in a combination of at least two kinds thereof at an arbitrary mixing ratio.

The amount of the solvent is not particularly limited. Usually, 3 or more times and 40 or less times a weight of the compound represented by Formula (1) are preferred.

The reaction temperature is not particularly limited, insofar as the desired reaction may proceed. The reaction temperature is usually set at 0° C. or more and 150° C. or less, or at a boiling temperature of the solvent or less.

As to a method of post-processing of a reaction mixture containing the compound represented by Formula (2), which is obtained by reacting the compound represented by Formula (1) with water under a basic condition, there is no particular limitation, insofar as the compound that is represented by Formula (2) and the desired product is not decomposed. In the following, the specific example of the method of post-processing will be described.

The compound represented by Formula (2), which is obtained by reacting the compound represented by Formula (1) and water under a basic condition, is present as a salt in the reaction mixture. When the salt is precipitated in the reaction mixture, the precipitate may be collected by filtration. On the other hand, when the salt is not precipitated, an organic solvent capable of separating from water is added to conduct liquid separation, and thereby impurities may be removed. Before the liquid separation is conducted, the solvent may be distilled off under reduced pressure, or water or an aqueous solution containing sodium chloride may be added.

When an acid is added to the salt collected by filtration, the salt contained in the separated and purified reaction mixture, or the salt contained in an untreated reaction mixture, the compound represented by Formula (2) is obtained by conversion.

Examples of acids added include organic acids such as methanesulfonic acid or toluenesulfonic acid, sulfonic acid, and inorganic acids such as hydrochloric acid, hydrobromic acid, or sulfuric acid.

The amount of the acid is not particularly limited insofar as it is 1 equivalent to the number of total moles of a base used in the reaction and generated ammonia.

As to a method of taking out the compound that is prepared by adding acid and represented by Formula (2), when the compound is precipitated from the reaction mixture, a precipitate may be collected by filtration. Furthermore, irrespective of the precipitation, the compound may be extracted with an organic solvent. When the extracted organic layer is concentrated to remove the solvent under reduced pressure, the compound is obtained. Before the concentration under reduced pressure, sodium sulfate or magnesium sulfate may be used to dewater. Thus obtained compound may be purified by recrystallization, reprecipitation, washing with a solvent, or distillation, according to a required level of purity.

A solvent that is used in the recrystallization, reprecipitation, or washing with solvent is not particularly limited insofar as the compound represented by Formula (2) is not decomposed.

Specific examples of the solvent that is used in the recrystallization, reprecipitation, or washing with solvent include water, halogen solvents, such as dichloromethane, chloroform or 1,2-dichloroethane, aromatic solvents, such as benzene, toluene, xylene, or anisole, ether solvents, such as diethyl ether, diisopropyl ether, 1,2-dimethoxyethane, tetrahydrofuran, or dioxane, alcohol solvents, such as methanol, ethanol, or isopropyl alcohol, hydrocarbon solvents, such as heptane, hexane, or cyclohexane, ester solvents, such as ethyl acetate, isopropyl acetate, or butyl acetate, and nitrile solvents, such as acetonitrile, or propionitrile. These solvents may be used singularly or in a combination of at least two kinds thereof at an arbitrary mixing ratio.

The amount of the solvent may be set according to a desired level of yield and purity without particular limitation. Usually, the usage amount of the solvent is preferably 1 times or more and 40 times or less a weight of the compound represented by Formula (2).

In the method for producing a fluorine-containing pyrazolecarboxylic acid derivative represented by Formula (2) of the present invention, among compounds represented by Formulae (1) and (2), compounds where R2 is a hydrogen atom are preferred, compounds where R2 is a hydrogen atom, and Rf is an alkyl group having 1 to 3 carbon atoms that is substituted by at least one fluorine atom are more preferred, and compounds where R2 is a hydrogen atom, Rf is a trifluoromethyl group, a difluoromethyl group, a chlorodifluoromethyl group, a pentafluoroethyl group or a heptafluoropropyl group, and R1 is an alkyl group having 1 to 6 carbon atoms are still more preferred, and compounds where R2 is a hydrogen atom, Rf is a trifluoromethyl group and R1 is an alkyl group having 1 to 6 carbon atoms are further preferred.

The method for producing a fluorine-containing pyrazolecarboxylic acid derivative represented by Formula (2) of the present invention preferably includes a process where a compound represented by Formula (1) is produced from a compound represented by Formula (3) below and a compound represented by Formula (4) below. Thereby, a compound represented by Formula (2) may be produced more efficiently.

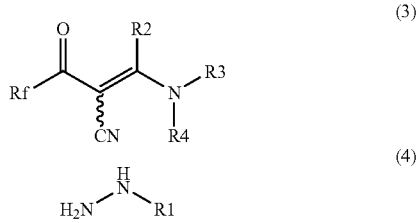

In the following, the method for producing a compound represented by Formula (1) will be described.

In the beginning, the compound represented by Formula (3) will be described.

Rf in Formula (3) has the same definition as the Rf in Formula (1).

R2 in Formula (3) has the same definition as the R2 in Formula (1).

R3 and R4 in Formula (3) are independent from each other.

An alkyl group having 1 to 6 carbon atoms in R3 or R4 in Formula (3) has the same definition as the alkyl group having 1 to 6 carbon atoms for the Rf in Formula (1).

A cycloalkyl group having 3 to 6 carbon atoms for R3 or R4 in Formula (3) has the same definition as the cycloalkyl group having 3 to 6 carbon atoms for the R1 in Formula (1).

An aryl group that may be substituted in R3 or R4 in Formula (3) has the same definition as the aryl group that may be substituted for the R2 in Formula (1).

An arylalkyl group that may be substituted for R3 or R4 in Formula (3) has the same definition as the arylalkyl group that may be substituted for the R1 in Formula (1).

A substituent group of an acyl group having 1 to 6 carbon atoms that may be substituted for R3 or R4 in Formula (3) has the same definition as the substituent of the arylalkyl group that may be substituted for the R1 in Formula (1).

Examples of the acyl group in the acyl group having 1 to 6 carbon atoms that may be substituted for R3 or R4 in Formula (3) include a formyl group, a methylcarbonyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, an isoamylcarbonyl group, a 3-methyl-2-butylcarbonyl group, a tert-pentylcarbonyl group, a neo-pentylcarbonyl group, a 2-pentylcarbonyl group and a 3-pentylcarbonyl group.

R3 and R4 in Formula (3) may be an atomic group that forms a 5- or 6-membered ring structure containing 0 or 1 heteroatom. Specific examples of the 5- or 6-membered ring structure include a pyrrolidino group, a piperidino group and a morpholino group.

The compound represented by Formula (3) may be a compound having any one of a trans-form and a cis-form, or a compound where a trans-form and a cis-form are mixed at an arbitrary mixing ratio. That is, the form thereof is not particularly limited.

As the compound represented by Formula (3), those that are appropriately produced according to a producing method described below may be used.

In the following, compounds represented by Formula (4) will be described.

R1 in Formula (4) has the same definition as the R1 in Formula (1).

A compound represented by Formula (4) may be a commercially available one or one produced according to a known method.

A compound represented by Formula (1) may be produced by reacting a compound represented by Formula (3) and a compound represented by Formula (4). The compound represented by Formula (1) is a novel compound. In the following, a producing method thereof will be described.

The amount of the compound represented by Formula (4) is not particularly limited insofar as it is 0.9 equivalent or more to a compound represented by Formula (3). However, the amount may be set 0.9 equivalent or more and 10 equivalent or less from the viewpoint of economic efficiency.

In the reaction of the compound represented by Formula (3) and the compound represented by Formula (4), any one of a method where the compound represented by Formula (3) is charged in the compound represented by Formula (4) and a method where the compound represented by Formula (4) is charged in the compound represented by Formula (3) may be adopted. As a charging form, powder charging, dropping and so on may be cited. At this time, the compound represented by Formula (3) or (4) may be used by dissolving or suspending in an appropriate solvent.

In the reaction, a solvent may be used. The solvent used is not particularly limited insofar as the reaction is forwarded. Specific examples of the solvent used include halogen solvents, such as dichloromethane, chloroform or 1,2-dichloroethane, aromatic solvents, such as benzene, toluene, xylene, or anisole, ether solvents, such as diethyl ether, diisopropyl ether, 1,2-dimethoxyethane, tetrahydrofuran, or dioxane, hydrocarbon solvent, such as heptane, hexane, or cyclohexane, ester solvents, such as ethyl acetate, isopropyl acetate, or butyl acetate, amide solvents, such as N-methyl-2-pyrrolidone, N,N-dimethylformamide, or N,N-dimethylacetamide, urea solvents, such as 1,3-dimethyl-2-imidazolidinone, or 1,3-dimethyl-3,4,5,6-tetrahydro-2(1H)-pyrimidinone, sulfoxide solvents, such as dimethylsulfoxide, ketone solvents, such as methyl isobutyl ketone, and water. These solvents may be used singularly or in a combination of at least two kinds thereof at an arbitrary mixing ratio.

The amount of the solvent is usually preferably a weight 3 times or more and 40 times or less a weight of the compound represented by Formula (3) without particular limitation.

The reaction temperature is not particularly limited insofar as a desired reaction may be forwarded. Usually, the reaction temperature is set at −10° C. or more and 150° C. or less or a boiling temperature of the solvent or less.

A post-processing of the reaction mixture that contains the compound represented by Formula (1) and is obtained by reacting the compound represented by Formula (3) and the compound represented by Formula (4) may be conducted without particular limitation insofar as the compound represented by Formula (1) is not decomposed. In the following, the specific example of the method of the post-processing will be described.

As to the reaction mixture when a two-layer solvent constituted from an organic solvent incompatible with water and water is the reaction solvent, when the liquid separation is conducted, the organic layer containing the compound represented by Formula (1) may be obtained.

As to the reaction mixture when a homogeneous solvent constituted of an organic solvent compatible with water and water is a reaction solvent, after the organic solvent is distilled off under reduced pressure, the compound represented by Formula (1) may be extracted with an organic solvent incompatible with water.

As to the reaction mixture when an organic solvent incompatible with water is a reaction solvent, the reaction mixture is concentrated under reduced pressure to remove the solvent, thereby the compound represented by Formula (1) may be obtained. Alternatively, before the solvent is distilled off, a liquid separation described below may be conducted.

As to the reaction mixture when an organic solvent compatible with water is a reaction solvent, the solvent may be distilled off under reduced pressure and thereby the compound represented by Formula (1) is obtained. After the solvent is distilled off, with an organic solvent incompatible with water added, a liquid separation described below may be conducted. At that time, water may be replaced with an aqueous solution such as an acidic aqueous solution, an alkaline aqueous solution, or saline.

As to the reaction mixture when water is the reaction solvent, when the compound represented by Formula (1) is precipitated, the precipitate may be collected by filtration. When the compound is not precipitated, an organic solvent incompatible with water may be added to extract.

The organic layer containing the compound represented by Formula (1) may be washed with water, an acidic aqueous solution, an alkaline aqueous solution, or saline. The times of washing, and an order of washing are not particularly limited insofar as the compound is not decomposed.

The acidic aqueous solution or the alkaline aqueous solution that is used to wash is not particularly limited insofar as the compound represented by Formula (1) is not decomposed. Usually, examples thereof include acidic aqueous solutions such as an aqueous solution of hydrochloric acid or an aqueous solution of sulfuric acid, and alkaline aqueous solutions such as an aqueous solution of sodium hydrogen carbonate, an aqueous solution of sodium carbonate, an aqueous solution of sodium hydroxide, an aqueous solution of potassium hydrogen carbonate, an aqueous solution of potassium carbonate, or an aqueous solution of potassium hydroxide.

The organic layer containing the compound represented by Formula (1) may be dewatered with sodium sulfate or magnesium sulfate.

The organic layer containing the compound represented by Formula (1) may be used as it is in a hydrolysis process as a next process. Furthermore, after the solvent is distilled off under reduced pressure, the compound may be hydrolyzed.

Processes such as distillation, recrystallization, reprecipitation, or washing with solvent may be applied to improve the purity of the compound represented by Formula (1).

The solvent that is used at the time of recrystallization, reprecipitation or washing with solvent is not particularly limited insofar as the compound represented by Formula (1) is not decomposed.

Specific examples of the solvent that is used in the recrystallization, reprecipitation and solvent washing include halogen solvents, such as dichloromethane, chloroform, or 1,2-dichloroethane, aromatic solvents, such as benzene, toluene, xylene or anisole, ether solvents, such as diethyl ether, diisopropyl ether, 1,2-dimethoxyethane, tetrahydrofuran, or dioxane, alcohol solvents, such as methanol, ethanol, or isopropyl alcohol, hydrocarbon solvents, such as heptane, hexane, or cyclohexane, ester solvents, such as ethyl acetate, isopropyl acetate, or butyl acetate, nitrile solvents, such as acetonitrile, or propionitrile, ketone solvents, such as methyl isobutylketone, and water. The solvents may be used singularly or in a combination of at least two kinds thereof at an arbitrary mixing ratio.

The amount of the solvent may be set according to a desired level of yield and purity without particular limitation. Usually, the amount of the solvent is preferably a weight 1 times or more and 40 times or less a weight of the compound represented by Formula (1).

When the compound represented by Formula (3) and the compound represented by Formula (4) are reacted, in addition to the compound represented by Formula (1), a compound represented by the following Formula (7):

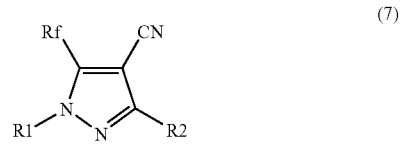

(7)

wherein, in Formula (7), Rf, R1 and R2 have the same definitions as the Rf, R1 and R2 in Formula (1), may be generated.

The compound represented by Formula (7) may be separated from the compound represented by Formula (1) by liquid separation, distillation, recrystallization, reprecipitation or solvent washing.

For example, when the compound where, in Formula (3), Rf is a trifluoromethyl group, R2 is a hydrogen atom, and R3 and R4 respectively represent a methyl group and the compound where, in Formula (4), R1 is a methyl group are reacted in a mixed solvent of toluene and water at a reaction temperature of 15° C. or less, a mixture of the compound represented by Formula (1) and the compound represented by Formula (7) is obtained. When the reaction mixture is subjected to liquid separation, the compound represented by Formula (1) is partitioned mainly in an organic layer and the compound represented by Formula (7) is partitioned mainly in a water layer. That is, the compound represented by Formula (1) is conveniently purified.

In the method for producing a fluorine-containing pyrazolecarbonitrile derivative represented by Formula (1), among compounds represented by Formulae (3) and (4), compounds where R2 is a hydrogen atom are preferred, compounds where R2 is a hydrogen atom, and Rf is an alkyl group having 1 to 3 carbon atoms that is substituted with at least one fluorine atom are more preferred, compounds where R2 is a hydrogen atom, R3 and R4 respectively represent independently an alkyl group having 1 to 6 carbon atoms, a cycloalkyl group having 3 to 6 carbon atoms, or an atomic group that forms a 5- or 6-membered ring containing 0 or 1 heteroatom with the nitrogen atom to which R3 and R4 are bonded are more preferred, compounds where R2 is a hydrogen atom, Rf is a trifluoromethyl group, R1 is an alkyl group having 1 to 6 carbon atoms, R3 and R4 each represent a methyl group, or one of R3 and R4 represents a methyl group and the other one thereof represents a cyclohexyl group, or R3 and R4 represent an atomic group that forms a pyrrolidino group or a morpholino group together with a nitrogen atom to which R3 and R4 are bonded, and compounds where R2 is a hydrogen atom, Rf is a difluoromethyl group, a chlorodifluoromethyl group, a pentafluoroethyl group or a heptafluoropropyl group, R1 is an alkyl group having 1 to 6 carbon atoms, and R3 and R4 each represent a methyl group are still more preferred.

The compound represented by Formula (3) in the present invention may be produced from a compound represented by the following Formula (5) and a compound represented by the following Formula (6). The method in the invention for producing a fluorine-containing pyrazolecarboxylic acid derivative represented by Formula (2) preferably further includes a process for producing the compound represented by Formula (3) from the compound represented by Formula (5) and the compound represented by Formula (6).

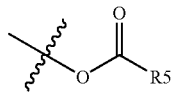

(5)

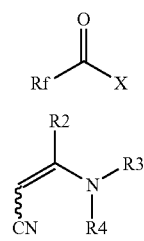

(6)

In the following, the method for producing the compound represented by Formula (3) will be described.

In the beginning, the compound represented by Formula (5) will be described.

Rf in Formula (5) has the same definition as the Rf in Formula (1).

A halogen atom in X in Formula (5) represents a fluorine atom, a chlorine atom, a bromine atom and an iodine atom.

A carbonyloxy group in X in Formula (5) represents a substituent group represented by Formula (8):

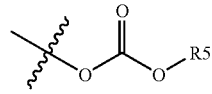

(8)

wherein, R5 represents an alkyl group that may be substituted with a halogen atom and has 1 to 6 carbon atoms, or a substituent group represented by Formula (9):

(9)

wherein R5 is the same as that described above.

A halogen atom in R5 in Formulae (8) and (9) has the same definition as the halogen atom in X in Formula (5).

An alkyl group having 1 to 6 carbon atoms for R5 in Formulae (8) and (9) has the same definition as the alkyl group having 1 to 6 carbon atoms in the Rf in Formula (1). Furthermore, the alkyl groups may be substituted with a halogen atom at one or more sites and is not particularly limited insofar as a desired acyl group is introduced. When at least two sites are substituted with a halogen atom, same kind or two or more kinds halogen atoms may substitute without particular restriction insofar as a desired acyl group may be introduced.

Examples of the compound represented by Formula (5) include, for example, trifluoroacetic acid, trifluoroacetic anhydride, trifluoroacetyl chloride, difluoroacetic acid, chlorodifluoroacetic acid, pentafluoropropionic acid and heptafluorobutyric acid. These may be commercially available products or those produced according to a known method.

In the following, compounds represented by Formula (6) will be described.

R2 in Formula (6) has the same definition as the R2 in Formula (1).

R3 and R4 in Formula (6) have the same definitions as the R3 and R4 in Formula (3).

The compound represented by Formula (6) may be a compound having any one of a trans-form and a cis-form, or a compound where a trans-form and a cis-form are mixed at an arbitrary mixing ratio. That is, the form thereof is not particularly limited.

Examples of the compound represented by Formula (6) include, for example, 3-dimethylamino-acrylonitrile, 3-cyclohexyl(methyl)amino-acrylonitrile, 3-pyrrolidino-acrylonitrile and 3-morpholino-acrylonitrile. The compounds may be commercially available ones or those produced with reference to JP-A No. 55-130950 or U.S. Pat. No. 3,966,791.

In the following, the method for producing the compound that is obtained by reacting the compound represented by Formula (5) and the compound represented by Formula (6) and represented by Formula (3) will be described.

In the following, a reaction where X in Formula (5) is a halogen atom will be described.

The amount of the compound represented by Formula (5) is not particularly limited insofar as the usage amount is 1 equivalent or more to the compound represented by Formula (6). However, the amount is preferably 1 equivalent or more and 3 equivalents or less from the viewpoint of economic efficiency.

When the compound represented by Formula (5) and the compound represented by Formula (6) are reacted, a base is preferably used.

The base used is an organic base or an inorganic base.

Specific examples of the organic base include tertiary amines, such as triethylamine, tributylamine, trioctylamine, diisopropylethylamine, 1,4-diazabicyclo[2.2.2]octane, or 1,8-diazabicyclo[5.4.0]-7-undecene, and aromatic amines, such as pyridine, collidine, lutidine, or 4-dimethylaminopyridine. Specific examples of the inorganic base include sodium hydrogen carbonate, potassium hydrogen carbonate, sodium carbonate, and potassium carbonate. These may be used singularly or in a combination of at least two kinds thereof at an arbitrary mixing ratio.

An equivalent of the base used is not particularly limited insofar as it is 1 equivalent or more to the compound represented by Formula (6). However, it is preferred to be 1 equivalent or more and 5 equivalents or less from the viewpoint of economic efficiency.

A solvent may be used in a reaction. The solvent used in the reaction is not particularly limited insofar as the solvent does not react with the compound represented by Formula (5).

Specific examples of the solvent include aprotic solvents, such as halogen solvents such as dichloromethane, chloroform, or 1,2-dichloroethane, aromatic solvents such as benzene, toluene, xylene or anisole, hydrocarbon solvents such as hexane, heptane, or cyclohexane, ester solvents such as ethyl acetate, butyl acetate, or isopropyl acetate, ether solvents such as diethyl ether, diisopropyl ether, 1,2-dimethoxyethane, tetrahydrofuran, or dioxane, nitrile solvents such as acetonitrile, or propionitrile, or ketone solvents such as methyl isobutyl ketone. The solvents may be used singularly or in a combination of at least two kinds thereof at an arbitrary mixing ratio.

The amount of a solvent is not particularly limited. However, usually a weight 3 times or more and 40 times or less to a weight of Formula (6) is preferred.

The reaction temperature is not particularly limited insofar as it is set so that the respective compounds may not be decomposed. However, usually it is set at −30° C. or more and 150° C. or less or at a boiling temperature of a solvent or less.

When X of the compound represented by Formula (5) is a halogen atom, the compound where Rf in Formula (5) is an alkyl group having 1 to 3 carbon atoms that is substituted by at least one fluorine atom is preferably adapted. More preferably, the compound represented by Formula (5) is trifluoroacetyl chloride or trifluoroacetyl fluoride.

In the following, the reaction when X in Formula (5) is a hydroxy group will be described.

The amount of the compound represented by Formula (5) is not particularly limited insofar as the amount is 1 equivalent or more to a compound represented by a formula (6). However, the amount is preferably 1 equivalent or more and 3 equivalents or less from the viewpoint of economic efficiency.

When X in Formula (5) is a hydroxy group, a halogenation agent or an imidazolination agent is preferably used.

Specific examples of the halogenation agent include thionyl chloride, oxalyl chloride, phosgene, phosphorus oxychloride, phosphorus trichloride, phosphorus pentachloride, oxalyl bromide, thionyl bromide, and phosphorus tribromide.

The amount of the halogenation agent is not particularly limited insofar as the amount is 1 equivalent or more to the compound represented by Formula (5). However, the amount is preferably 1 equivalent or more and 3 equivalents or less from the viewpoint of economic efficiency.

A halogenation agent may be used by adding a formamide derivative such as a dimethyl formamide and thereby converting into a Vilsmeier reagent.

A Vilsmeier reagent is a salt containing a compound represented by the following Formula (10):

wherein, R6 and R7 are independent from each other and represent an allyl group having 1 to 6 carbon atoms, and Y represents a halogen atom.

An alkyl group having 1 to 6 carbon atoms in R6 and R7 in Formula (10) has the same definition as the allyl group having 1 to 6 carbon atoms for Rf in Formula (1).

Furthermore, specific examples of an imidazolination agent include N,N'-carbonyldiimidazole.

The amount of the imidazolination agent is not particularly limited insofar as the amount thereof is 1 equivalent or more to a compound represented by Formula (5). However, the amount is preferably 1 equivalent or more and 3 equivalents or less from the viewpoint of economic efficiency.

When the compound represented by Formula (5) and the compound represented by Formula (6) are reacted, a base is preferably used.

The base used is an organic base or an inorganic base.

Specific examples of the organic base include tertiary amines, such as triethylamine, tributylamine, trioctylamine, diisopropylethylamine, 1,4-diazabicyclo[2.2.2]octane, or 1,8-diazabicyclo[5.4.0]-7-undecene, and aromatic amines, such as pyridine, collidine, lutidine, or 4-dimethylaminopyridine. Specific examples of the inorganic base include sodium hydrogen carbonate, potassium hydrogen carbonate, sodium carbonate, and potassium carbonate. These bases may be used singularly or in a combination of at least two kinds thereof at an arbitrary mixing ratio.

A usage amount of the base used is not particularly limited insofar as it is 2 equivalents or more to the compound represented by Formula (6). However, it is preferred to be 2 equivalents or more and 5 equivalents or less from the viewpoint of economic efficiency.

A solvent may be used in the reaction. The solvent that is used in the reaction is not particularly limited insofar as it does not react with the compound represented by Formula (5).

Specific examples of the solvent include aprotic solvents, such as halogen solvents such as dichloromethane, chloroform, or 1,2-dichloroethane, aromatic solvents such as benzene, toluene, xylene or anisole, hydrocarbon solvents such as hexane or heptane, ester solvents such as ethyl acetate, butyl acetate, or isopropyl acetate, ether solvents such as diethyl ether, diisopropyl ether, 1,2-dimethoxyethane, tetrahydrofuran, or dioxane, nitrile solvents such as acetonitrile, or propionitrile, or ketone solvents such as methyl isobutyl ketone.

The amount of a solvent is not particularly limited. However, usually a weight that is 3 times or more and 40 times or less a weight of the compound represented by Formula (6) is preferred.

The reaction temperature is not particularly limited insofar as it is set so that the respective compounds may not be decomposed. However, usually, it is set at −30° C. or more and 150° C. or less or at a boiling temperature of a solvent or less.

As to a charging method of the reagent, it is preferred to add a halogenation agent at the last to a solvent that contains the compound represented by Formula (5), the compound represented by Formula (6) and the base. Furthermore, a formamide derivative may be added as requires to a solvent that contains the compound represented by Formula (5), the compound represented by Formula (6) and the base. According to the charging method, a yield of the compound represented by Formula (3) is much improved.

When X of the compound represented by Formula (5) is a hydroxy group, in the present invention, Rf in Formula (5) is preferably an alkyl group having 1 to 3 carbon atoms that is substituted with at least one fluorine atom. More preferably, the compound represented by Formula (5) is trifluoroacetic acid, difluoroacetic acid, chlorodifluoroacetic acid, pentafluoropropionic acid, or heptafluorobutyric acid.

In the following, a reaction when X in Formula (5) is a carbonyloxy group will be described.

The amount of the compound represented by Formula (5) is not particularly limited insofar as it is 1 equivalent or more to the compound represented by Formula (6). However, it is preferred to be 1 equivalent or more and 3 equivalents or less from the viewpoint of economic efficiency.

When the compound represented by Formula (5) and the compound represented by Formula (6) are reacted, a base may be used but not necessarily.

The base used is an organic base or an inorganic base.

Specific examples of the organic base include tertiary amines, such as triethylamine, tributylamine, trioctylamine, diisopropylethylamine, 1,4-diazabicyclo[2.2.2]octane, or 1,8-diazabicyclo[5.4.0]-7-undecene, and aromatic amines, such as pyridine, collidine, lutidine, or 4-dimethylaminopyridine. Specific examples of the inorganic base include sodium hydrogen carbonate, potassium hydrogen carbonate, sodium carbonate, and potassium carbonate. These bases may be used singularly or in a combination of at least two kinds thereof at an arbitrary mixing ratio.

The amount of the base is not particularly limited. However, it is preferred to be 5 equivalents or less from the viewpoint of economic efficiency.

A solvent may be used in a reaction. The solvent that is used in the reaction is not particularly limited insofar as it does not react with the compound represented by Formula (5).

Specific examples of the solvent include aprotic solvents, such as halogen solvents such as dichloromethane, chloroform, or 1,2-dichloroethane, aromatic solvents such as benzene, toluene, xylene or anisole, hydrocarbon solvents such as hexane or heptane, ester solvents such as ethyl acetate, butyl acetate, or isopropyl acetate, ether solvents such as diethyl ether, diisopropyl ether, 1,2-dimethoxyethane, tetrahydrofuran, or dioxane, nitrile solvents such as acetonitrile, or propionitrile, or ketone solvents such as methyl isobutyl ketone.

The amount of the solvent is not particularly limited. However, usually, a weight that is 3 times or more and 40 times or less a weight of the compound represented by Formula (6) is preferred.

The reaction temperature is not particularly limited insofar as it is set so that the respective compounds may not be decomposed. However, usually, it is set at −30° C. or more and 150° C. or less or at a boiling temperature of a solvent or less.

When X of the compound represented by Formula (5) is a carbonyloxy group, a symmetric compound (represented by —O(C=O)Rf) where Rf in Formula (5) is an alkyl group having 1 to 3 carbon atoms that is substituted with at least one fluorine atom, X is a substituent represented by Formula (8), and R5 in Formula (8) is Rf may be adapted to the invention. More preferably, the compound represented by Formula (5) is trifluoroacetic anhydride.

In the following, a post-processing process will be described. The post-processing processes are common through the respective reactions when X is a halogen atom, a hydroxy group, and a carbonyloxy group.

The reaction mixture that contains the compound represented by Formula (3) and is obtained by reacting the compound represented by Formula (5) and the compound represented by Formula (6) may be washed with water, an alkaline aqueous solution, an acidic aqueous solution or saline.

An alkaline aqueous solution or an acidic aqueous solution that is used to wash is not particularly limited insofar as the compound represented by Formula (3) is not decomposed. Usually, alkaline aqueous solutions, such as an aqueous solution of sodium hydrogen carbonate, an aqueous solution of sodium carbonate, an aqueous solution of sodium hydroxide, an aqueous solution of potassium hydrogen carbonate, an aqueous solution of potassium carbonate, or an aqueous solution of potassium hydroxide, and acidic aqueous solutions, such as an aqueous solution of hydrochloric acid or an aqueous solution of sulfuric acid are cited.

The number of times of washing the reaction mixture is not particularly limited.

The reaction mixture containing the compound represented by Formula (3) that is obtained by washing with water, an alkaline aqueous solution or an acidic aqueous solution may be dewatered with sodium sulfate or magnesium sulfate.

The reaction mixture that contains the compound represented by Formula (3) and is obtained by washing with water, an alkaline aqueous solution, an acidic aqueous solution, or saline or the reaction mixture dewatered with sodium sulfate or magnesium sulfate may be used as it is in a process of rendering pyrazole in a following process. Furthermore, after the solvent is distilled off, the reaction mixture may be used in a following step. Still furthermore, after recrystallization, reprecipitation, washing with a solvent, or distillation is applied to purify, the reaction mixture may be used in a following step.

The solvent that is used in recrystallization, reprecipitation or washing with solvent is not particularly limited insofar as the compound represented by Formula (3) is not decomposed.

Specific examples of the solvent that is used in the recrystallization, reprecipitation and solvent washing include water, halogen solvents, such as dichloromethane, chloroform, or 1,2-dichloroethane, aromatic solvents, such as benzene, toluene, xylene or anisole, ether solvents, such as diethyl ether, diisopropyl ether or 1,2-dimethoxyethane, alcohol solvents, such as methanol, ethanol, or isopropyl alcohol, hydrocarbon solvents, such as heptane, hexane, or cyclohexane, ester solvents, such as ethyl acetate, isopropyl acetate, or butyl acetate, nitrile solvents, such as acetonitrile, or propionitrile, and ketone solvents, such as methyl isobutyl ketone. The solvents may be used singularly or in a combination of at least two kinds thereof at an arbitrary mixing ratio.

The amount of the solvent may be set according to a desired level of yield and purity without particular limitation. Usually, the amount of the solvent is a weight preferably 1 times or more and 40 times or less a weight of the compound represented by Formula (3).

In the method for producing compounds represented by Formula (3) in the invention, among compounds represented by Formulae (5) and (6), compounds where R2 is a hydrogen atom are preferred, compounds where R2 is a hydrogen atom, and Rf is an alkyl group having 1 to 3 carbon atoms, in which Rf is substituted with at least one fluorine atom, are more preferred, compounds where R2 is a hydrogen atom, R3 and R4 each independently represent an alkyl group having 1 to 6 carbon atoms, or a cycloalkyl group having 3 to 6 carbon atoms, or an atomic group which forms a 5- or 6-membered ring containing 0 or 1 heteroatom with a nitrogen atom to which R3 and R4 are bonded, and X is a halogen atom, a hydroxyl group or —O(C=O)Rf are still more preferred, compounds where R2 is a hydrogen atom, Rf is a trifluoromethyl group, R1 is an alkyl group having 1 to 6 carbon atoms, R3 and R4 respectively represent a methyl group, or one of R3 and R4 represents a methyl group and the other one thereof represents a cyclohexyl group, or R3 and R4 represent a group of atoms forming a pyrrolidino group or a morpholino group together with a nitrogen atom to which R3 and R4 are bonded, X is a halogen atom, a hydroxyl group or —O(C=O)Rf are more preferred, and compounds where R2 is a hydrogen atom, Rf is a difluoromethyl group, a chlorodifluoromethyl group, a pentafluoroethyl group or a heptafluoroethyl group, R1 is an alkyl group having 1 to 6 carbon atoms, both R3 and R4 are a methyl group, X is a halogen atom, a hydroxyl group or —O(C=O)Rf are still more preferred.

According to the present invention that was shown above, the novel fluorine-containing pyrazolecarbonitrile derivative represented by Formula (1), the method for producing the same, the method for producing the fluorine-containing pyrazolecarboxylic acid derivative therewith, and the novel fluorine-containing pyrazolecarboxylic acid derivative may be provided.

EXAMPLES

In the following, the present invention will be described in more detail with reference to examples, but the present invention is not limited thereto.

Hereinafter, 3-dimethylamino-acrylonitrile is referred as Compound (I), 3-(dimethylamino)-2-trifluoroacetylacrylonitrile is referred as Compound (II), 1-methyl-3-(trifluoromethyl)-1H-pyrazole-4-carbonitrile is referred as Compound (III), 1-methyl-5-(trifluoromethyl)-1H-pyrazole-4-carbonitrile is referred as Compound (IV), 1-methyl-3-(trifluoromethyl)-1H-pyrazole-4-carboxylic acid is referred as Compound (V), 1-methyl-5-(trifluoromethyl)-1H-pyrazole-4-carboxylic acid is referred as Compound (VI), 3-pyrrolidino-2-trifluoroacetylacrylonitrile is referred as a compound (VII), 3-cyclohexyl(methyl)amino-2-trifluoroacetylacrylonitrile is referred as Compound (VIII), 3-morpholino-2-trifluoroacetylacrylonitrile is referred as Compound (IX), 3-dimethylamino-2-difluoroacetylacrylonitrile is referred as Compound (X), 1-methyl-3-(difluoromethyl)-1H-pyrazole-4-carbonitrile is referred as Compound (XI), 1-methyl-5-(difluoromethyl)-1H-pyrazole-4-carbonitrile is referred as Compound (XII), 1-methyl-3-(difluoromethyl)-1H-pyrazole-4-carboxylic acid is referred as Compound (XIII), 3-dimethylamino-2-(pentafluoroethylcarbonyl)acrylonitrile is referred as Compound (XIV), 1-methyl-3-(pentafluoroethyl)-1H-pyrazole-4-carbonitrile is referred as Compound (XV), 1-methyl-3-(pentafluoroethyl)-1H-pyrazole-4-carboxylic acid is referred as Compound (XVI), 3-dimethylamino-2-(heptafluoropropylcarbonyl)acrylonitrile is referred as Compound (XVII), 1-methyl-3-(heptafluoropropyl)-1H-pyrazole-4-carbonitrile is referred as Compound (XVIII), 1-methyl-3-(heptafluoropropyl)-1H-pyrazole-4-carboxylic acid is referred as Compound (XIX), 3-dimethylamino-2-(chlorodifluoromethylcarbonyl)acrylonitrile is referred as Compound (XX), 1-methyl-3-(chlorodifluoromethyl)-1H-pyrazole-4-carbonitrile is referred as Compound (XXI), 1-methyl-5-(chlorodifluoromethyl)-1H-pyrazole-4-carbonitrile is referred as Compound (XXII), and a high-performance liquid chromatography is referred as HPLC.

Example 1

Acylation: Synthesis of Compound (II) using Trifluoroacetic Acid and Phosgene

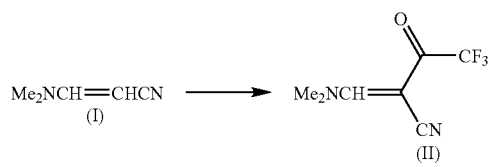

Under a nitrogen atmosphere, 5.24 g of trifluoroacetic acid was added dropwise to 80 ml of toluene containing 4.65 g of Compound (I) having a purity of 95% by weight and 9.30 g of triethylamine, while cooling with ice. Subsequently, 40 ml of toluene containing 5.00 g of phosgene was added dropwise. After completing the dropwise addition, the temperature of the resultant was increased to room temperature, and the resultant was stirred for 2 hours. Nitrogen was then allowed to flow through the reaction solution for 1 hour, and the reaction yield was observed by HPLC. The result showed Compound (II) was quantitatively generated. In the next place, 120 ml of water was added for liquid separation, and the organic layer was washing with 120 ml of saturated sodium bicarbonate solution and dried with sodium sulfate. After removing sodium sulfate, the solvent was distilled off under reduced pressure. Diisopropyl ether was added to the residue, and the mixture was stirred. The precipitate was collected by filtration and 7.32 g of a tan solid as Compound (II) (yield: 83%).

Material data of Compound (II)

$^1$H NMR (CDCl$_3$) δ3.38 (3H, s), 3.58 (3H, s), 7.96 (1H, s)

$^{13}$C NMR (CDCl$_3$) δ39.45, 48.89, 75.08, 116.03, 116.69 (q, J=290.4 Hz), 159.61, 176.25 (q, J=34.3 Hz)

IR (KBr) 1140, 1186, 1624, 2210 cm$^{-1}$

Melting point: 68.4 to 69.3° C.

Example 2

Cyclization: Conversion from Compound (II) to Compound (III) Part One Thereof

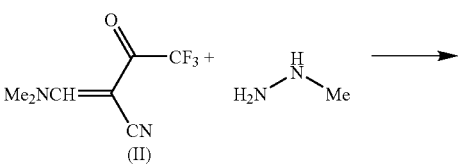

-continued

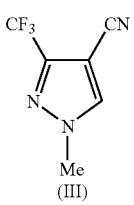

85 ml of water was added to 170 ml of toluene in which 17.0 g of Compound (II) was dissolved, followed by cooling with ice. Thereto, 90.1 g of a 5.6% by weight aqueous solution of methyl hydrazine was added dropwise. After completion of the adding, the solution was stirred at the same temperature for 3 hours and thereby an organic layer and an aqueous layer were separated. When the respective layers were observed with the HPLC at this time, 78% of Compound (III) and 2% of Compound (II) were formed in the organic layer and 2% of Compound (III) and 11% of Compound (IV) were formed in the aqueous layer. Next, the organic layer was concentrated under reduced pressure to remove a solvent, followed by purifying by distilling. When a fraction of distillate of 8 mmHg and 96 to 106° C. was batched off, 9.70 g of Compound (III) was obtained as a colorless transparent oily substance (yield: 63%).

Material Data of Compound (III)
$^1$H NMR (CDCl$_3$) δ4.03 (3H, s), 7.91 (1H, s)
$^{13}$C NMR (CDCl$_3$) δ40.10, 91.12, 110.43, 119.55 (q, J=269.9 Hz), 137.11, 143.64 (q, J=39.2 Hz)

Material Data of Compound (IV)
$^1$H NMR (CDCl$_3$) δ4.08 (3H, s), 7.83 (1H, s)

Example 3

Cyclization: Conversion from Compound (II) to Compound (III) Part Two Thereof 20 ml of toluene containing 2.00 g of Compound (II) was added dropwise to 20.6 g of a 2.8% by weight aqueous solution of methyl hydrazine while cooling with ice. After stirring at the same temperature for 3 hours, an organic layer and an aqueous layer were separated. When the respective layers were observed with the HPLC at this time, 81% of Compound (III) and 1% of Compound (IV) were formed in the organic layer and 1% of Compound (III) and 9% of Compound (IV) were formed in the aqueous layer. Next, the organic layer was washed with 10% by weight of hydrochloric acid and concentrated under reduced pressure to remove the solvent, thereby 1.64 g of Compound (III) having a purity of 90.5% by weight was obtained (yield: 81%).

Example 4

Cyclization: Conversion from Compound (II) to Compound (III) Part Three Thereof

With various kinds of solvents shown in Table 1 below, according to a method shown below, a reaction yield of each of conversion reactions from Compound (II) to Compound (III) was calculated.
20 ml of a predetermined solvent containing 2.00 g of Compound (II) was added dropwise to 6.00 g of a 9.7% by weight aqueous solution of methyl hydrazine, while cooling with ice. After the completing the dropwise addition, the solution was stirred for 2 hours at the same temperature. When an aqueous solvent was used, 2.00 g of a compound (II) was charged in powder into a 2.2% by weight aqueous solution of methyl hydrazine under ice cooling. When a dimethyl sulfoxide solvent was used, a reaction was conducted not under ice cooling but at room temperature.

A method for calculating a reaction yield is as follows. When the reaction mixture was separated into two layers, yields of the respective layers were observed with the HPLC after an organic layer and an aqueous layer were separated, and a total value thereof was calculated as the reaction yield. When a reaction mixture was homogeneous, the reaction mixture was observed as it is with the HPLC and the reaction yield was calculated. Regarding the aqueous solvent, acetonitrile was added to the reaction mixture with oil droplets to homogenize, followed by observing with the HPLC, further followed by calculating the reaction yield. Results thereof are shown in Table 1 below.

TABLE 1

| Solvent | Yield of Compound (III) | Yield of Compound (IV) |
| --- | --- | --- |
| Toluene | 85% | 8% |
| Xylene | 85% | 11% |
| Anisole | 81% | 11% |
| Acetonitrile | 84% | 12% |
| Methanol | 87% | 12% |
| Ethanol | 82% | 9% |
| Isopropyl alcohol | 84% | 13% |
| Tetrahydrofuran | 81% | 14% |
| 1,2-dimethoxyethane | 82% | 12% |
| Chloroform | 87% | 11% |
| Ethyl acetate | 77% | 17% |
| N,N-dimethylformamide | 80% | 9% |
| 1,3-dimethyl-2-imidazolyzinone | 84% | 10% |
| Dimethylsulfoxide | 72% | 23% |
| Pyridine | 83% | 10% |
| Methyl isobutyl ketone | 79% | 15% |
| Water | 81% | 14% |

Example 5

Hydrolysis: Conversion from Compound (III) to Compound (V) Part One Thereof

[Kagaku 24]

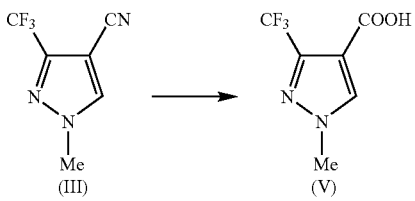

A mixture of 0.20 g of Compound (III), 2 ml of water, 2 ml of acetic acid and 2 ml of sulfuric acid was allowed to react at an internal temperature of 100° C. for 5 hours. After cooling, ethyl acetate and water were added to conduct liquid separation. The organic layer was dried with sodium sulfate, followed by removing sodium sulfate, and the organic layer was concentrated under reduced pressure. Toluene was added to the residue, followed by further concentration under reduced pressure. Diisopropyl ether and hexane were added to a residue, followed by stirring, and a precipitate was collected by filtration. The resulted pale yellow solid was Compound (V), and the yield was 0.15 g (68%).

Material Data of Compound (V)

$^1$H NMR (DMSO-$d_6$) δ3.93 (3H, s), 8.45 (1H, s)

Example 6

Hydrolysis: Conversion from Compound (III) to Compound (V) Part Two Thereof 0.50 g of Compound (III) having purity of 98.1% by weight was dissolved in 4 ml of ethanol, followed by further adding 2.0 g of a 32% by weight aqueous solution of sodium hydroxide, further followed by reacting at a external temperature of 85° C. for 4 hours. The reaction solution was observed by HPLC after cooling, and the result showed that the reaction yield of Compound (V) was 98%.

Example 7

Hydrolysis: Conversion from Compound (III) to Compound (V) Part Three Thereof 0.50 g of Compound (III) having purity of 98.1% by weight was dissolved in 4 ml of methanol, followed by further adding 2.0 g of a 32% by weight aqueous solution of sodium hydroxide, further followed by reacting at an external temperature of 75° C. for 4 hours. The reaction solution was observed by HPLC after cooling, and the result showed that the reaction yield of Compound (V) was 99% or more.

Example 8

Hydrolysis: Conversion from Compound (III) to Compound (V) Part Four Thereof 0.50 g of Compound (III) having purity of 98.1% by weight was dissolved in 4 ml of water, followed by further adding 2.0 g of a 32% by weight aqueous solution of sodium hydroxide, further followed by reacting at an external temperature of 100° C. for 4 hours. The reaction solution was observed by HPLC after cooling, and the result showed that the reaction yield of Compound (V) was 99% or more.

Example 9

Synthesis from Compound (I) up to Compound (V) Part One Thereof

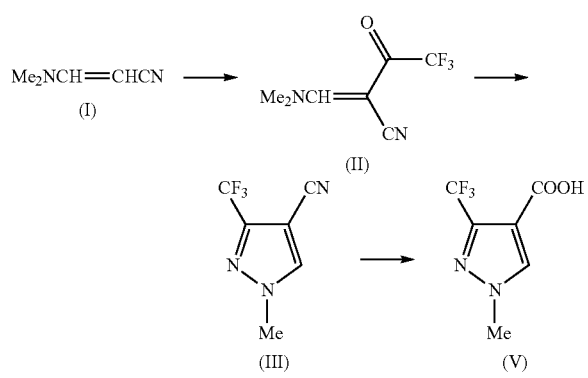

220 ml of toluene containing 17.8 g of Compound (I) having purity of 95% by weight and 35.5 g of triethylamine was cooled to an internal temperature of 4° C. Thereto, 20.0 g of trifluoroacetic acid was added dropwise, followed by cooling to an internal temperature of 5° C. Thereto, 110 ml of toluene containing 22.3 g of oxalyl chloride was added dropwise at 20° C. or less. After completing the dropwise addition, the temperature of the resultant was increased to room temperature, followed by stirring for 6 hours. The reaction solution was observed by HPLC, and the result showed that the reaction yield of Compound (II) was 30.7 g (91%). Next, the organic layer was washed twice with 330 ml of water and once with 330 ml of a saturated sodium bicarbonate solution. When 304.7 g of the organic layer was observed by HPLC, 27.3 g of Compound (II) was contained (yield: 81%).

Then, 165 g of water was added to 303.3 g (27.2 g as Compound (II)) of the organic layer, followed by cooling to an internal temperature of 3° C. Thereto, 32.6 g of a 40% by weight aqueous solution of methyl hydrazine was added dropwise over 40 min, followed by stirring for 3 hours, further followed by conducting liquid separation. Furthermore, the separated organic layer was washed sequentially with 330 ml of 0.5N hydrochloric acid and 330 ml of a saturated sodium bicarbonate solution. Next, the organic layer was concentrated off under reduced pressure to remove the solvent, and thereby 20.3 g (yield: 74%) of Compound (III) having purity of 90.4% by weight was obtained as a tan oily material. In the oily material, 0.3 g (yield: 1%) of Compound (IV) was found contained as an impurity.

In the next place, to 20.3 g of Compound (III) having purity of 90.4% by weight, 160 ml of water and 74.6 g of a 32% by weight aqueous solution of sodium hydroxide were added, followed by increasing the temperature of the reaction solution to an internal temperature of 75° C., further followed by allowing reacting for 4 hours. After cooling to room temperature, the reaction solution was observed by HPLC, 20.4 g of Compound (V) (yield: 99% or more) and 0.1 g of Compound (VI) were found generated. The pH of the reaction solution was adjusted to 1.8 with concentrated hydrochloric acid, and a precipitate was collected by filtration. Compound (VI) was removed in a filtrate, and a resulted solid was a pale yellow Compound (V). Yield was 19.6 g (96%).

Example 10

Synthesis from Compound (I) up to Compound (V) Part Two Thereof 908 g of toluene containing 62.1 g of Compound (I) having purity of 95% by weight and 124.2 g of triethylamine was cooled to an internal temperature of 5° C. Thereto, 70.0 g of trifluoroacetic acid was added dropwise at an internal temperature of 15° C. or less. Then, the solution was cooled to an internal temperature of 5° C., followed by introducing 94 g of phosgene at 25° C. or less. After stirring at room temperature for 2 hr, nitrogen was allowed to flow through the reaction solution 1.5 hours and thereby excessive phosgene was removed. The reaction solution was observed by HPLC, and the results showed that 118.0 g of a compound (II) was generated (yield: 99% or more). To the reaction solution, 1000 g of water was added, followed by stirring for 1 hour, and further followed by conducting liquid separation. The separated organic layer was washed with 1000 g of a 5% by weight sodium bicarbonate solution, and thereby 1015.6 g of the toluene solution containing 111.1 g (yield: 94%) of a compound (II) was obtained.

Then, 324.3 g of a 9.8% by weight aqueous solution of methyl hydrazine was cooled with ice to an internal temperature of 5° C., and 1007.3 g (content of Compound (II):110.2 g) of the toluene solution was added dropwise with an internal temperature maintained at 10° C. or less. After the completion of the dropwise addition, the solution was stirred at an internal temperature of 6° C. for 2 hours, and the organic layer and the aqueous layer were separated. The separated organic layer was washed with 300 g of 10% by weight hydrochloric acid. Then, the solvent was distilled off under reduced pressure, and thereby 91.4 g (yield: 82%) of Compound (III) having purity of 90.5% by weight was obtained as brownish oily material. The oily substance contained 1.8 g (yield: 2%) of Compound (IV) as an impurity.

To 90.4 g of Compound (III) having purity of 90.5% by weight, 723 g of water and 225.5 g of a 47.3% by weight aqueous solution of sodium hydroxide were sequentially added, followed by heating to an internal temperature of 75° C. After stirring at the same temperature for 4 hours, a temperature was decreased to room temperature. When the reaction solution was observed by HPLC at this time, the result showed that 90.6 g (yield: 99% or more) of a compound (V) and 2.3 g of a compound (VI) were generated. Next, after the pH of the reaction solution was adjusted to 3.3 with concentrated hydrochloric acid, a precipitate was collected by filtration. Compound (VI) was removed in a filtrate. An obtained solid white was Compound (V). A yield amount was 88.2 g (yield: 97%).

Example 11

Cyclization: Synthesis of 1-ethyl-3-(trifluoromethyl)-1H-pyrazole-4-carbonitrile

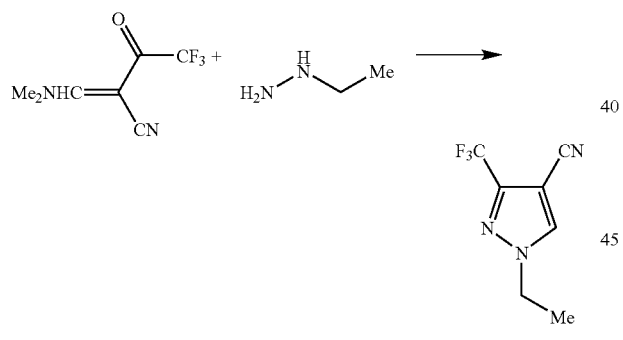

After 1.00 g of Compound (II) was dissolved in 20 ml of toluene, thereto 8 ml of water was added, followed by cooling with ice. Thereto, 2 ml of water containing 0.63 g of ethyl hydrazine was added dropwise, followed by stirring for 5 hours while cooling with ice. Next, liquid separation was conducted and the separated organic layer was dried with magnesium sulfate. After magnesium sulfate was removed, the solvent was distilled off under reduced pressure, thereby 0.67 g of a mixture of 1-ethyl-3-(trifluoromethyl)-1H-pyrazole-4-carbonitrile and 1-ethyl-5-(trifluoromethyl)-1H-pyrazole-4-carbonitrile at a ratio of 84:16 (calculated from $^1$H NMR) was obtained as a yellow oily substance. Yield was 57%.

Material data of 1-ethyl-3-(trifluoromethyl)-1H-pyrazole-4-carbonitrile
$^1$H NMR (CDCl$_3$) δ1.57 (3H, t, J=7.3 Hz), 4.28 (2H, q, J=7.3 Hz), 7.91 (1H, s)

Material data of 1-ethyl-5-(trifluoromethyl)-1H-pyrazole-4-carbonitrile
$^1$H NMR (CDCl$_3$) δ1.53 (3H, t, J=7.3 Hz), 4.34 (2H, q, J=7.3 Hz), 7.86 (1H, s)

Example 12

Hydrolysis: Synthesis of 1-ethyl-3-(trifluoromethyl)-1H-pyrazole-4-carboxylic acid

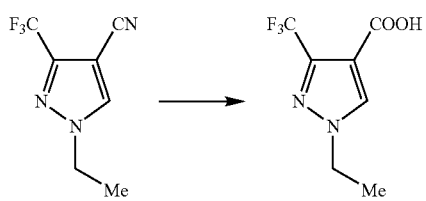

To 0.67 g of the nitrile body obtained in Example 11, 5 g of water and 2.52 g of 32% by weight sodium hydroxide were added, followed by allowing reacting at an external temperature of 85° C. for 2 hours. The reaction solution was acidified with concentrated hydrochloric acid, followed by adding ethyl acetate for liquid separation. To the separated organic layer, sodium sulfate was added to dry, followed by filtering. The filtrate was concentrated under reduced pressure, followed by adding hexane to the residue, further followed by collecting a precipitate by filtration. The resulted yellow solid was the compound shown in the title and a yield amount thereof was 0.51 g (yield: 81%). An isomer of the compound shown in the title was not detected by $^1$H NMR.

Material data of 1-ethyl-3-(trifluoromethyl)-1H-pyrazole-4-carboxylic acid
$^1$H NMR (CDCl$_3$) δ1.56 (3H, t, J=7.3 Hz), 4.25 (2H, d, J=7.3 Hz), 8.07 (1H, s)

Example 13

Acylation: Synthesis of Compound (VII) from Trifluoroacetic Acid and Oxalyl Chloride

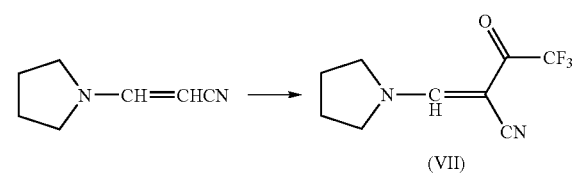

Under a nitrogen atmosphere, 8.89 g of trifluoroacetic acid was added dropwise while cooling with ice to 150 ml of toluene containing 10.0 g of 3-pyrrolidino-acrylonitrile and 15.78 g of triethylamine. Next, 9.89 g of oxalyl chloride was added dropwise, followed by further stirring for 2 hours while cooling with ice. Water was added to the reaction solution for liquid separation, and the separated organic layer was washed with a saturated sodium bicarbonate solution, followed by drying with magnesium sulfate. After magnesium sulfate was removed, the solvent was distilled off under reduced pressure. Isopropanol was added to the residue to recrystallize and thereby an tan solid was obtained. As a result, 12.60 g of Compound (VII) shown in the title was obtained as a solid (yield: 74%).

$^1$H NMR (CDCl$_3$) δ2.02 (2H, quint, J=6.84 Hz), 2.15 (2H, quint, J=6.84 Hz), 3.80 (2H, t, J=6.84 Hz), 4.05 (2H, t, J=6.84 Hz), 8.15 (1H, s)

$^{13}$C NMR (CDCL$_3$) δ23.86, 25.35, 49.02, 56.44, 75.15, 116.47, 116.65 (q, J=290.47 Hz), 115.86, 175.68 (q, J=34.93 Hz)

IR (KBr) 947, 1127, 1212, 1597, 1680, 2201 cm$^{-1}$

Melting temperature: 91.1 to 95.4° C.

Example 14

Cyclization: Conversion from Compound (VII) to Compound (III)

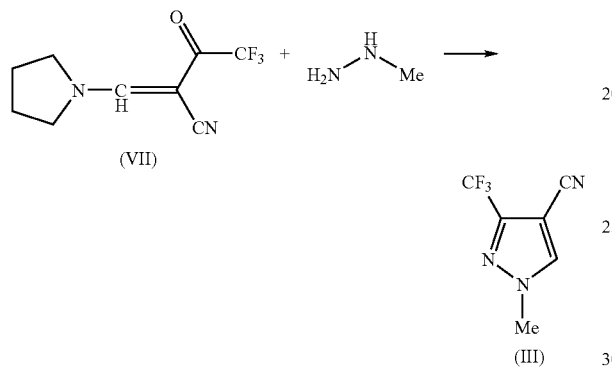

To 7.8 g of water containing 0.86 g of methyl hydrazine having a purity of 98% by weight, 20 ml of toluene was added, followed by cooling with ice. Thereto, 2.0 g of Compound (VII) was charged, followed by stirring for 2 hours at the same temperature. The reaction solution was observed by HPLC, the result showed that Compound (III) was generated by 56% and Compound (IV) was generated by 21%. The yields are total value of an organic layer and an aqueous layer.

Example 15

Acylation: Synthesis of Compound (VIII) from Trifluoroacetic Acid and Oxalyl Chloride

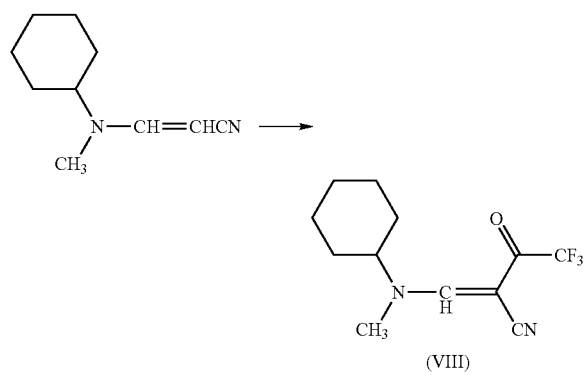

The reaction was conducted in a manner similar to Example 13 except that 3-cyclohexyl(methyl)amino-acrylonitrile was used in place of 3-pyrrolidino-acrylonitrile, and in place of adding isopropanol to a residue, ethanol was added. Compound (VIII) shown in the title was obtained as a drab solid, and the yield thereof was 71%.

$^1$H NMR (CDCl$_3$) δ1.16 (1H, m), 1.36 (2H, m), 1.53 (2H, m), 1.75 (1H, m), 1.95 (4H, m), 3.24 (3H, s: minor), 3.33 (1H, m), 3.47 (3H, s: major), 7.92 (1H, s: minor), 8.05 (1H, s: major)

IR (KBr) 1145, 1165, 1202, 1590, 1672, 2205 cm$^{-1}$

Melting temperature: 127.7 to 129.1° C.

Example 16

Cyclization: Conversion from Compound (VIII) to Compound (III)

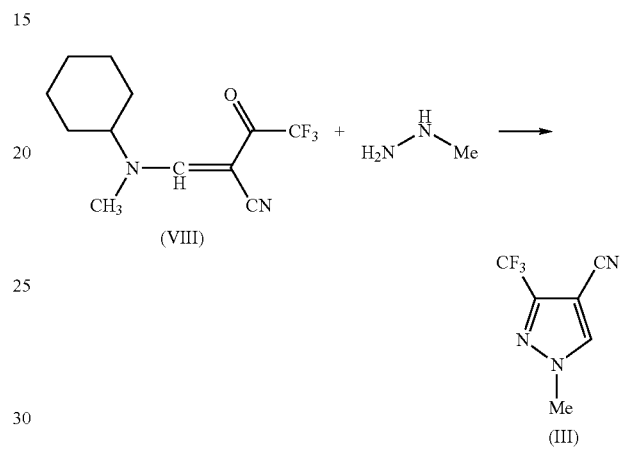

A reaction was conducted in a manner similar to Example 14 except that Compound (VII) was used in place of Compound (VIII). The reaction solution observed by HPLC, the result showed that the yield of Compound (III) was 65% and the yield of Compound (IV) was 25%. The yields thereof are a total value of an organic layer and an aqueous layer.

Example 17

Acylation: Synthesis of Compound (Ix) from Trifluoroacetic Acid and Oxalyl Chloride

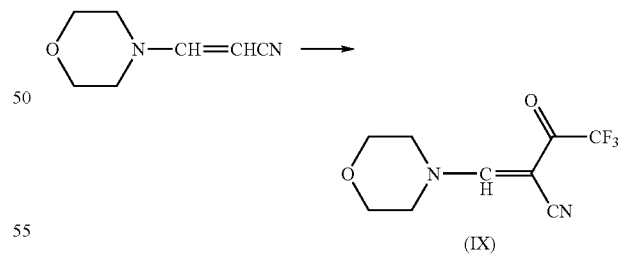

A reaction was conducted in a manner similar to Example 13 except that 3-morpholino-acrylonitrile was used in place of 3-pyrrolidino-acrylonitrile, and an operation of adding isopropanol to a residue to recrystallize was changed to an operation where a mixed solvent of ethyl acetate and diisopropyl ether was used to wash a precipitate. Compound (IX) shown in the title was obtained as a drab solid and the yield thereof was 74%.

$^1$H NMR (CDCl$_3$) δ3.66 (2H, m), 3.88 (4H, m), 4.22 (2H, m), 7.98 (1H, s)

$^{13}$C NMR (CDCL$_3$) δ48.1, 57.2, 65.9, 66.8, 74.8, 116.0, 116.7 (q, J=290.5 Hz), 157.8, 176.6 (q, J=34.9 Hz)

IR (KBr) 929, 942, 1115, 1146, 1191, 1215, 1355, 1599, 1686, 2204 cm$^{-1}$

Melting temperature: 112.2 to 113.8° C.

Example 18

Cyclization: Conversion from Compound (IX) to Compound (III)

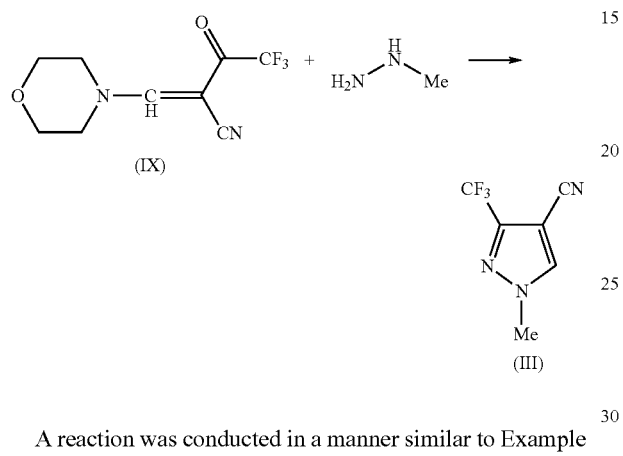

A reaction was conducted in a manner similar to Example 14 except that Compound (VII) was used in place of Compound (IX). The reaction solution was observed by HPLC, the result showed that the yield of Compound (III) was 80% and the yield of Compound (IV) was 12%. The yields thereof are a total value of an organic layer and an aqueous layer.

Example 19

Acylation: Synthesis of Compound (X) from Difluoroacetic Acid and Phosgene

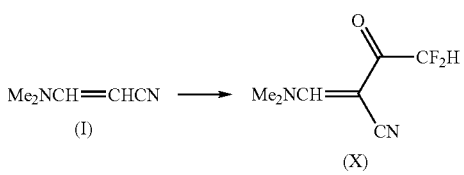

Under a nitrogen atmosphere, 10.00 g of Compound (I) having a purity of 95% and 20.05 g of triethylamine were added to 125 g of toluene, followed by cooling with ice. Thereto, 9.51 g of difluoroacetic acid was added dropwise, followed by cooling to 3° C. Thereto, 12.2 g of phosgene was introduced over about 20 min, followed by increasing to room temperature, further followed by stirring for 2 hours. At this time point, a reaction solution was observed by HPLC, the compound shown in the title was found generated at the yield of 94% (16.17 g). Thereto, water was added for liquid separation. Ethyl acetate was added to the separated aqueous layer to extract. The organic layers were combined and washed with a saturated sodium bicarbonate solution. Next, the organic layer was dried with magnesium sulfate, followed by filtering. The resulted filtrate was concentrated under reduced pressure, followed by adding diisopropyl ether, further followed by stirring, and a precipitate was collected by filtration. A resulted yellow solid was 13.15 g (76%) of Compound (X) shown in the title.

$^1$H NMR (CDCl$_3$) δ3.36 (3H, s), 3.50 (3H, s), 6.19 (1H, t, J=53.7 Hz), 7.93 (1H, s)

$^{13}$C NMR (CDCL$_3$) δ39.51, 48.89, 76.65, 109.39 (t=250.9 Hz), 117.44, 158.91, 182.60 (t, J=23.9 Hz)

IR (KBr) 867, 978, 1064, 1129, 1279, 1356, 1433, 1614, 1674, 2201 cm$^{-1}$

Melting temperature: 66.9 to 68.9° C.

Example 20

Cyclization: Conversion from Compound (X) to Compound (XI)

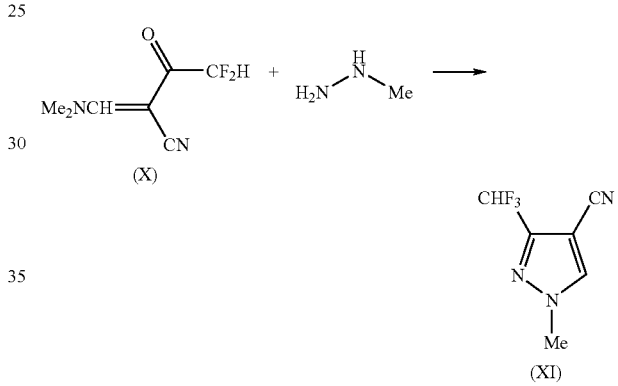

To 29 g of water containing 3.24 g of methyl hydrazine having a purity of 98% by weight while cooling with ice, 100 ml of a toluene solution containing Compound (X) was added dropwise under the same temperature, followed by stirring for 3 hours. Then, liquid separation was conducted, the separated organic layer was washed with 0.5 N hydrochloric acid, and followed by drying with magnesium sulfate. After magnesium sulfate was removed, the solvent was removed by concentrating the filtrate under reduced pressure. When the resulted brown solid (7.62 g) was observed by $^1$H NMR, it was found that Compound (XI)/Compound (XII)=95.7/4.3. Then, the brown solid was thoroughly washed with a mixed solvent of hexane and diisopropyl ether, and thereby Compound (XI) was obtained as a pale yellow solid (4.83 g, yield: 54%).

Material Data of Compound (XI)

$^1$H NMR (CDCl$_3$) δ3.99 (3H, s), 6.72 (1H, t, J=53.7 Hz), 7.88 (1H, s)

$^{13}$C NMR (CDCL$_3$) δ40.00, 90.49, 109.69 (t, J=236.2 Hz), 111.41, 136.98, 148.15 (t, J=29.4 Hz)

IR (KBr) 812, 854, 1036, 1091, 1169, 1190, 1349, 1545, 2241, 3162 cm$^{-1}$

Melting temperature: 39.0 to 40.9° C.

Material Data of Compound (XII)

$^1$H NMR (CDCl$_3$) δ4.06 (3H, s), 6.85 (1H, t, J=52.5 Hz), 7.79 (1H, s)

Example 21

Hydrolysis: Conversion from Compound (XI) to Compound (XIII)

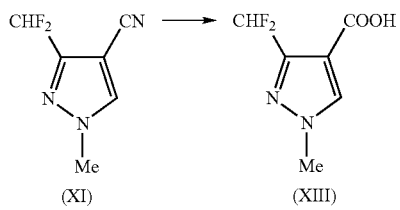

To 40 ml of water containing 3.56 g of sodium hydroxide, 4.0 g of Compound (XI) was added, followed by allowing reacting at an external temperature of 95° C. for 4 hr. After the reaction came to completion, the reaction mixture was acidified by adding concentrated hydrochloric acid while cooling with ice. Then, the solution was stirred for 1 hour at room temperature and a precipitate was filtered. The resulted white solid was Compound (XIII) (4.11 g). The yield was 92%.

Material Data of Compound (XIII)

$^1$H NMR (DMSO-d$_6$) δ3.91 (3H, s), 7.21 (1H, t, J=53.7 Hz), 8.33 (1H, s)

Example 22

Acylation: Synthesis of Compound (XIV) from Pentafluoropropionic Acid and Phosgene

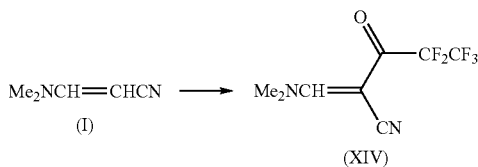

Under a nitrogen atmosphere, 10.00 g of Compound (I) having a purity of 95% and 20.05 g of triethylamine were added to 210 g of toluene, followed by cooling with ice. Thereto, 16.25 g of pentafluoropropionic acid was added dropwise, followed by cooling to 5° C. Thereto, 12.8 g of phosgene was introduced over about 20 min, followed by heating to room temperature, further followed by stirring for 2 hours. Thereto, water and ethyl acetate were added for liquid separation, and the separated organic layer was washed with a saturated sodium bicarbonate solution. The organic layer was dried with magnesium sulfate, followed by filtering. The resulted filtrate was concentrated under reduced pressure, diisopropyl ether was added thereto, followed by stirring, and further followed by collecting the precipitate by filtration. The resulted pale yellow solid was Compound (XIV) shown in the title (21.03 g, 88%).

$^1$H NMR (CDCl$_3$) δ3.39 (3H, s), 3.56 (3H, s), 7.98 (1H, s)

$^{13}$C NMR (CDCL$_3$) δ39.51, 49.11, 76.69, 108.39 (tq, J=38.6 Hz, 268.4 Hz), 115.88, 118.05 (tq, J=34.0, 286.8 Hz), 160.10, 178.13 (t, J=25.7 Hz)

IR (KBr) 1117, 1155, 1220, 1310, 1354, 1612, 1681, 2202 cm$^{-1}$

Melting temperature: 101.1 to 102.5° C.

Example 23

Cyclization: Conversion from Compound (XIV) to Compound (XV)

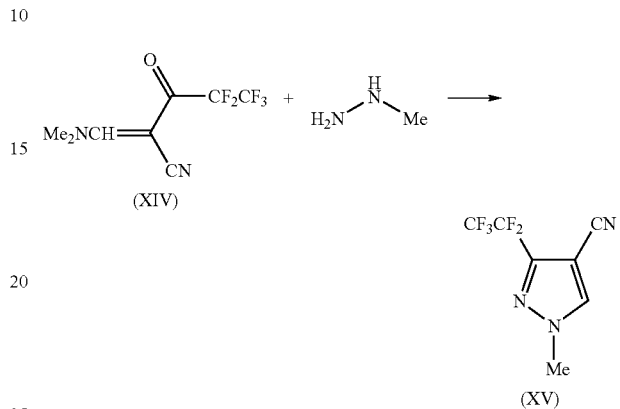

To 20.5 g of water containing 2.28 g of methyl hydrazine having a purity of 98% by weight, 100 ml of toluene was added, followed by cooling with ice, and further followed by charging 10.0 g of Compound (XIV). After stirring at the same temperature for 3 hours, liquid separation was conducted. The separated organic layer was washed with 0.5N hydrochloric acid and dried with magnesium sulfate. After magnesium sulfate was removed, the filtrate was concentrated under reduced pressure to remove a solvent, and thereby 7.78 g of Compound (XV) was obtained as a yellow oily substance. Thus-obtained Compound (XV) was, without further purifying, used in a following hydrolysis process. Part of Compound (XV) was purified by silica gel chromatography and thereby substance data shown below were obtained.

$^1$H NMR (CDCl$_3$) δ4.05 (3H, s), 7.95 (1H, s)

$^{13}$C NMR (CDCL$_3$) δ40.62, 93.00, 110.60 (tq, J=40.6, 253.7 Hz), 111.26, 118.96 (tq, J=36.8, 286.8 Hz), 138.46 (t, J=38.6 Hz), 142.63 (t, J=29.4 Hz)

IR (KBr) 741, 969, 1018, 1100, 1153, 1207, 1339, 1542, 2244 cm$^{-1}$

Example 24

Hydrolysis: Conversion from Compound (XV) to Compound (XVI)

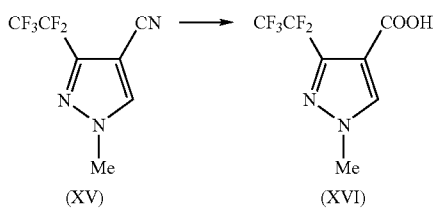

60 ml of water containing 5.61 g of Compound (XV) obtained in example 23 and 3.49 g of sodium hydroxide was reacted at an external temperature of 95° C. for 4 hours. The reaction mixture was cooled to room temperature, followed by adding concentrated hydrochloric acid to the mixed solution to acidify. After the mixed solution was further stirred for 1 hour, a precipitate was collected by filtration. The resulted white solid (5.53 g) was Compound (XVI). A total yield from Compound (XIV) was 76%.

$^1$H NMR (DMSO-$d_6$) δ3.95 (3H, s), 8.49 (1H, s), $^{13}$C NMR (DMSO-$d_6$) δ39.59, 110.60 (tq, J=38.6, 250.3 Hz), 114.59, 118.87 (tq, J=37.7, 285.0 Hz), 138.16, 138.19 (q, J=29.4 Hz), 161.70,

IR (KBr) 747, 958, 1116, 1208, 1548, 1704, 3439 cm$^{-1}$,

Melting temperature: 136.4 to 143.5° C.

Example 25

Acylation: Synthesis of Compound (XVII) from Heptafluorobutyric Acid and Phosgene

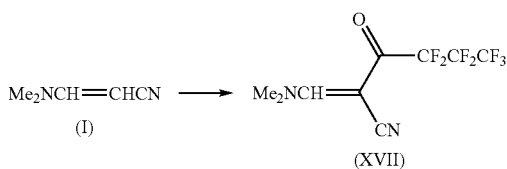

Under a nitrogen atmosphere, 10.00 g of Compound (I) having a purity of 95% by weight and 20.05 g of triethylamine were added to 280 g of toluene, followed by cooling with ice. Thereto, 21.21 g of heptafluorobutyric acid was added dropwise, followed by cooling to 6° C. Thereto, 12.3 g of phosgene was introduced thereinto over about 20 min, followed by heating to room temperature, further followed by stirring for 2 hr. Thereto, water was added for liquid separation, and the separated organic layer was washed with a saturated sodium bicarbonate solution. Furthermore, the organic layer was dried with magnesium sulfate, followed by filtering. The resulted filtrate was concentrated under reduced pressure, followed by adding diisopropyl ether, further followed by stirring, followed by collecting a precipitate by filtration. Thereby, 25.01 g (86%) of Compound (XVII) shown in the title was obtained as a pale yellow solid.

$^1$H NMR (CDCl$_3$) δ3.39 (3H, s), 3.56 (3H, s), 8.01 (1H, s), $^{13}$C NMR (CDCl$_3$) δ39.27, 48.87, 76.67, 108.46 (m), 110.07 (tt, J=31.17, 267.49 Hz), 115.92, 117.36 (tq, J=33.09, 286.79 Hz), 160.32, 177.51 (t, J=23.9 Hz),

IR (KBr) 876, 1119, 1209, 1226, 1316, 1344, 1426, 1606, 1674, 2208 cm$^{-1}$,

Melting temperature: 73.9 to 75.4° C.

Example 26

Cyclization: Conversion from Compound (XVII) to Compound (XVIII)

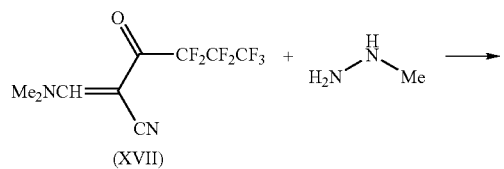

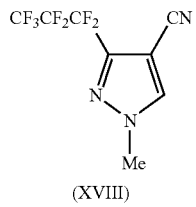

To 17.0 g of water containing 1.89 g of methyl hydrazine having a purity of 98% by weight, 100 ml of toluene was added, followed by cooling with ice, and further followed by charging 10.0 g of Compound (XVII). The solution was stirred at the same temperature for 3 hours and subjected to liquid separation. The separated organic layer was washed with 0.5N hydrochloric acid, followed by drying with magnesium sulfate. After magnesium sulfate was removed, the filtrate was concentrated under reduced pressure to remove a solvent, and, thereby, Compound (XVIII) was obtained as a yellow oily substance (7.83 g). Thus obtained Compound (XVIII) was used in a following hydrolysis process without further purifying. Part of the compound (XVIII) was purified by silica gel chromatography and thereby material data shown below were obtained.

$^1$H NMR (CDCl$_3$) δ4.06 (3H, s), 7.94 (1H, s), $^{13}$C NMR (CDCl$_3$) δ40.62 (q, J=11.0 Hz), 93.34, 108.83 (m), 111.28, 112.00 (tt, J=33.1, 288.6 Hz), 118.11 (tq, J=34.0, 286.8 Hz), 138.20 (t, J=40.4 Hz), 142.71 (m),

IR (KBr) 745, 886, 1120, 1236, 1346, 1542, 2245 cm$^{-1}$,

Example 27

Hydrolysis: Conversion from Compound (XVIII) to Compound (XIX)

[Kagaku 42]

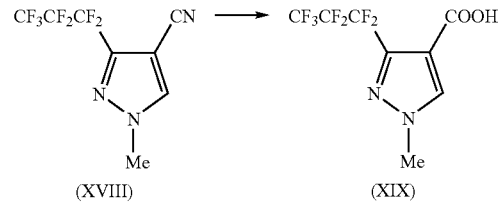

To 60 ml of water containing 2.92 g of sodium hydroxide, 30 ml of ethanol and 5.74 g of Compound (XVIII) obtained in example 26 were added, followed by reacting at an external temperature of 95° C. for 6 hr. The reaction mixture was cooled to room temperature, followed by concentrating to a volume about one half an initial volume thereof under reduced pressure. Then, water and chloroform were added for liquid separation. Concentrated hydrochloric acid was added to the separated aqueous layer, followed by stirring for 1 hour, further followed by collecting a precipitate by filtering. Compound (XIX) was obtained as a white solid (3.64 g). A total yield from Compound (XVII) of example 26 was 49%.

$^1$H NMR (DMSO-$d_6$) δ3.96 (3H, s), 8.49 (1H, s), $^{13}$C NMR (DMSO-$d_6$) δ39.57, 108.57 (tq, J=37.4, 264.7 Hz), 112.60 (tt, J=32.2, 253.7 Hz), 114.85, 117.78 (tq, J=34.0, 288.6 Hz), 138.22, 138.25 (q, J=32.5 Hz), 161.63,

IR (KBr) 887, 1118, 1227, 1546, 1710, 3435 cm$^{-1}$,

Melting temperature: 116.3 to 121.2° C.

Example 28

Acylation: Synthesis of Compound (XX) from Chlorodifluoroacetic Acid and Phosgene

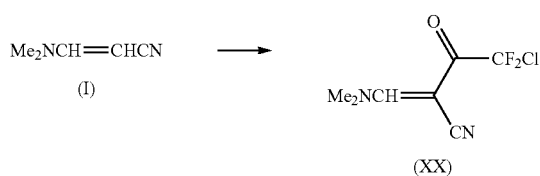

Under a nitrogen atmosphere, 10.00 g of Compound (I) having purity of 95% and 20.05 g of triethylamine were added to 170 g of toluene, followed by cooling with ice. Thereto, 12.93 g of chlorodifluoroacetic acid was added dropwise, followed by cooling to 5° C. Thereto, 12.3 g of phosgene was introduced thereinto over about 20 min, and the temperature of the mixture increased to room temperature, followed by stirring for 2 hours. Thereto, water was added for liquid separation, and the separated organic layer was washed with a saturated sodium bicarbonate solution. Furthermore, the organic layer was dried with magnesium sulfate, followed by filtering. The resulted filtrate was concentrated under reduced pressure, followed by adding diisopropyl ether and stirring, and a precipitate was collecting by filtration. Thereby, 17.20 g (83%) of Compound (XX) shown in the title was obtained as a pale yellow solid.

$^1$H NMR (CDCl$_3$) δ3.38 (3H, s), 3.55 (3H, s), 7.98 (1H, s),
$^{13}$C NMR (CDCl$_3$) δ39.35, 48.96, 73.82, 116.32, 119.83 (t, J=304.3 Hz), 160.14, 177.77 (t, J=28.5 Hz),
IR (KBr) 899, 981, 1155, 1351, 1427, 1613, 1685, 2202 cm$^{-1}$,
Melting temperature 72.3 to 73.5° C.

Example 29

Cyclization: Conversion from Compound (XX) to Compound (XXI)

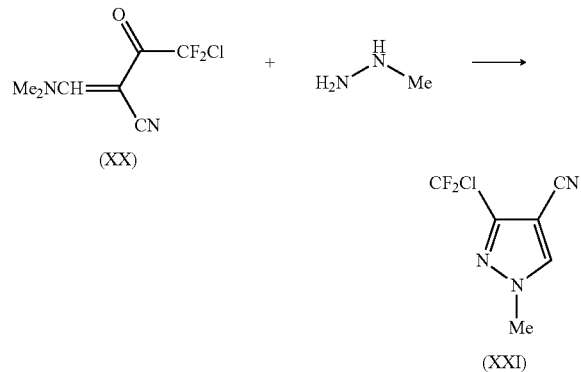

To 24 g of water containing 2.65 g of methyl hydrazine having purity of 98% by weight, 100 ml of toluene was added, followed by cooling with ice, and further followed by charging 10.0 g of Compound (XX), followed by stirring for 3 hours, further followed by subjecting to liquid separation. The separated organic layer was washed with 0.5N hydrochloric acid, followed by drying with magnesium sulfate. After magnesium sulfate was removed, the obtained filtrate was concentrated under reduced pressure. The resulted yellow oily substance (8.36 g) was observed by $^1$H NMR and found to be a mixture of Compound (XXI)/compound (XXII)= 97.3/2.7. That is, almost all thereof is a compound (XXI). Part of the compound (XXI) was purified by silica gel chromatography and thereby material data shown below were obtained.

Material Data of Compound (XXI)
$^1$H NMR (CDCl$_3$) δ4.02 (3H, s), 7.91 (1H, s),
$^{13}$C NMR (CDCl$_3$) δ39.99, 89.97, 110.58, 120.95 (t, J=285.9 Hz), 137.39, 147.88 (t, J=32.2 Hz),
IR (KBr) 629, 917, 1064, 1133, 1230, 1484, 1542, 2243 cm$^{-1}$, Material Data of Compound (XXII)
$^1$H NMR (CDCl$_3$) δ4.09 (3H, s), 7.81 (1H, s)

INDUSTRIAL APPLICABILITY

The present invention provide a novel fluorine-containing pyrazolecarbonitrile derivative and a method for the same. Since a reagent that is problematic from the viewpoint of safeness and waste disposition is not used, and an operation is convenient, the present invention is suitable as an industrial producing method as well. Furthermore, a resulted novel fluorine-containing pyrazolecarbonitrile derivative may be converted to an important raw material for agrihorticultural insecticides; accordingly it is a very useful production intermediate. From what was mentioned above, the usefulness of the invention is very high in medical and agricultural fields.

What is claimed is:
1. A fluorine-containing pyrazolecarbonitrile derivative represented by the following Formula (1):

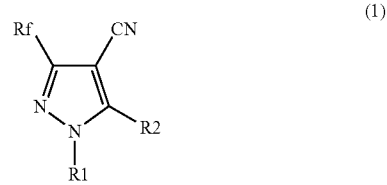

wherein, in Formula (1), Rf represents an alkyl group having 1 to 6 carbon atoms which is substituted by at least one fluorine atom, R1 represents an alkyl group having 1 to 6 carbon atoms, a cycloalkyl group having 3 to 6 carbon atoms, or an arylalkyl group which may be substituted, and R2 represents a hydrogen atom, an alkyl group having 1 to 6 carbon atoms, a cycloalkyl group having 3 to 6 carbon atoms, an aryl group which may be substituted, or an arylalkyl group which may be substituted.

2. The fluorine-containing pyrazolecarbonitrile derivative according to claim 1, wherein, in Formula (1), R2 represents a hydrogen atom.

3. The fluorine-containing pyrazolecarbonitrile derivative according to claim 2, wherein, in Formula (1), Rf represents a trifluoromethyl group, a difluoromethyl group, a chlorodifluoromethyl group, a pentafluoroethyl group, or a heptafluoropropyl group, and R1 represents an alkyl group having 1 to 6 carbon atoms.

4. A method for producing a fluorine-containing pyrazole-carboxylic acid derivative represented by the following Formula (2), the method comprising reacting a compound represented by the following Formula (1) with water:

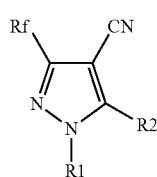
(1)

wherein, in Formula (1), Rf represents an alkyl group having 1 to 6 carbon atoms which is substituted by at least one fluorine atom; R1 represents an alkyl group having 1 to 6 carbon atoms, a cycloalkyl group having 3 to 6 carbon atoms, or an arylalkyl group which may be substituted; and R2 represents a hydrogen atom, an alkyl group having 1 to 6 carbon atoms, a cycloalkyl group having 3 to 6 carbon atoms, an aryl group which may be substituted, or an arylalkyl group which may be substituted:

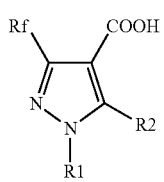
(2)

wherein, in Formula (2), Rf, R1 and R2 have the same definitions as those described above.

5. The method for producing a fluorine-containing pyrazolecarboxylic acid derivative according to claim 4, wherein, in compounds represented by Formulae (1) and (2), R2 represents a hydrogen atom.

6. The method for producing a fluorine-containing pyrazolecarboxylic acid derivative according to claim 5, wherein, in compounds represented by Formulae (1) and (2), Rf represents a trifluoromethyl group, a difluoromethyl group, a chlorodifluoromethyl group, a pentafluoroethyl group, or a heptafluoropropyl group, and R1 represents an alkyl group having 1 to 6 carbon atoms.

7. The method for producing a fluorine-containing pyrazolecarboxylic acid derivative represented by Formula (2) according to claim 4, which further includes producing a compound represented by Formula (1) according to claim 4, from a compound represented by the following Formula (3) and a compound represented by the following Formula (4):

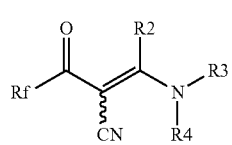
(3)

wherein, in Formula (3), Rf and R2 have the same definitions as those described in claim 4; R3 and R4 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or an atomic group that forms a 5- or 6-membered ring containing 0 or 1 heteroatom with the nitrogen atom to which R3 and R4 are bonded;

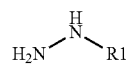
(4)

wherein, in Formula (4), R1 has the same definition as that described in claim 4.

8. The method for producing a fluorine-containing pyrazolecarboxylic acid derivative according to claim 7, wherein, in compounds represented by Formulae (1), (2), (3) and (4), R2 represents a hydrogen atom; and R3 and R4 each independently represent an alkyl group having 1 to 6 carbon atoms, or a cycloalkyl group having 3 to 6 carbon atoms, or R3 and R4 represent an atomic group that forms a 5- or 6-membered ring containing 0 or 1 heteroatom with the nitrogen atom to which R3 and R4 are bonded.

9. The method for producing a fluorine-containing pyrazolecarboxylic acid derivative according to claim 8, wherein, in compounds represented by Formulae (1), (2), (3) and (4), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

10. The method for producing a fluorine-containing pyrazolecarboxylic acid derivative according to claim 8, wherein, in compounds represented by Formulae (1), (2), (3) and (4), Rf represents a difluoromethyl group, a chlorodifluoromethyl group, a pentafluoroethyl group, or a heptafluoropropyl group, R1 represents an alkyl group having 1 to 6 carbon atoms, and R3 and R4 respectively represent a methyl group.

11. The method for producing a fluorine-containing pyrazolecarboxylic acid derivative represented by Formula (2) according to claim 7, which further includes producing a compound represented by Formula (3) from a compound represented by the following Formula (5) and a compound represented by the following Formula (6):

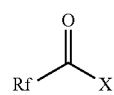
(5)

wherein, in Formula (5), Rf has the same definition as that described in claim 7, and X represents a halogen atom, a hydroxy group, or a carbonyloxy group;

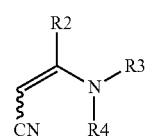
(6)

wherein, in Formula (6), R2, R3 and R4 have the same definitions as those described in claim 7.

12. The method for producing a fluorine-containing pyrazolecarboxylic acid derivative according to claim 11, wherein, in compounds represented by Formulae (1), (2), (3), (4), (5) and (6), R2 represents a hydrogen atom; and R3 and R4 each independently represent an alkyl group having 1 to 6 carbon atoms, or a cycloalkyl group having 3 to 6 carbon atoms, or R3 and R4 represent an atomic group that forms a 5- or 6-membered ring containing 0 or 1 heteroatom with the nitrogen atom to which R3 and R4 are bonded; and X represents a halogen atom, a hydroxy group or —O(C=O)Rf.

13. The method for producing a fluorine-containing pyrazolecarboxylic acid derivative according to claim 12, wherein, in compounds represented by Formulae (1), (2), (3), (4), (5) and (6), Rf represents a trifluoromethyl group; R1 represents an alkyl group having 1 to 6 carbon atoms; R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

14. The method for producing a fluorine-containing pyrazolecarboxylic acid derivative according to claim 12, wherein, in compounds represented by Formulae (1), (2), (3), (4), (5) and (6), Rf represents a difluoromethyl group, a chlorodifluoromethyl group, a pentafluoroethyl group, or a heptafluoropropyl group; R1 represents an alkyl group having 1 to 6 carbon atoms; and R3 and R4 respectively represent a methyl group.

15. A method for producing a fluorine-containing pyrazolecarbonitrile derivative represented by the following Formula (1), the method comprising reacting a compound represented by the following Formula (3) with a compound represented by the following Formula (4):

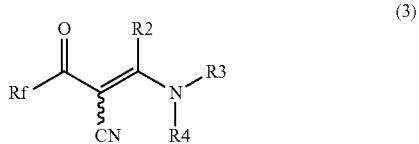

(3)

wherein, in Formula (3), Rf represents an alkyl group having 1 to 6 carbon atoms which is substituted by at least one fluorine atom; R2 represents a hydrogen atom, an alkyl group having 1 to 6 carbon atoms, a cycloalkyl group having 3 to 6 carbon atoms, an aryl group which may be substituted, or an arylalkyl group which may be substituted; and R3 and R4 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or R3 and R4 represent an atomic group that forms a 5- or 6-membered ring containing 0 or 1 heteroatom with the nitrogen atom to which R3 and R4 are bonded;

(4)

wherein, in Formula (4), R1 represents an alkyl group having 1 to 6 carbon atoms, a cycloalkyl group having 3 to 6 carbon atoms, or an arylalkyl group which may be substituted;

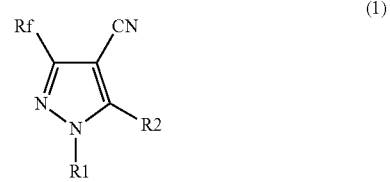

(1)

wherein, in Formula (1), Rf, R1 and R2 have the same definitions as those described above.

16. The method for producing a fluorine-containing pyrazolecarbonitrile derivative according to claim 15, wherein, in Formulae (1), (3) and (4), R2 represents a hydrogen atom; and R3 and R4 each independently represent an alkyl group having 1 to 6 carbon atoms, or a cycloalkyl group having 3 to 6 carbon atoms, or R3 and R4 represent an atomic group that forms a 5- or 6-membered ring containing 0 or 1 heteroatom with the nitrogen atom to which R3 and R4 are bonded.

17. The method for producing a fluorine-containing pyrazolecarbonitrile derivative according to claim 16, wherein, in compounds represented by Formulae (1), (3) and (4), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

18. The method for producing a fluorine-containing pyrazolecarbonitrile derivative according to claim 16, wherein, in compounds represented by Formulae (1), (3) and (4), Rf represents a difluoromethyl group, a chlorodifluoromethyl group, a pentafluoroethyl group, or a heptafluoropropyl group, R1 represents an alkyl group having 1 to 6 carbon atoms, and R3 and R4 respectively represent a methyl group.

19. The method for producing a fluorine-containing pyrazolecarbonitrile derivative represented by Formula (1) according to claim 15, which further includes producing a compound represented by Formula (3) from a compound represented by the following Formula (5) and a compound represented by the following Formula (6):

(5)

wherein, in Formula (5), Rf has the same definition as that described in claim 15, and X represents a halogen atom, a hydroxy group, or a carbonyloxy group;

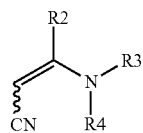

wherein, in Formula (6), R2, R3 and R4 have the same definitions as those described in claim 15.

20. The method for producing a fluorine-containing pyrazolecarbonitrile derivative according to claim 19, wherein, in compounds represented by Formulae (1), (3), (4), (5) and (6), R2 represents a hydrogen atom; R3 and R4 each independently represent an alkyl group having 1 to 6 carbon atoms, or a cycloalkyl group having 3 to 6 carbon atoms, or R3 and R4 represent an atomic group that forms a 5- to 6-membered ring containing 0 or 1 heteroatom with the nitrogen atom to which R3 and R4 are bonded; and X represents a halogen atom, a hydroxy group, or —O(C=O)Rf.

21. The method for producing a fluorine-containing pyrazolecarbonitrile derivative according to claim 20, wherein, in compounds represented by Formulae (1), (3), (4), (5) and (6), Rf represents a trifluoromethyl group; R1 represents an alkyl group having 1 to 6 carbon atoms; and R3 and R4 respectively represent a methyl group, or one of R3 and R4 represents a methyl group and the other one thereof represents a cyclohexyl group, or R3 and R4 represent an atomic group that forms a pyrrolidino group or a morpholino group together with the nitrogen atom to which R3 and R4 are bonded.

22. The method for producing a fluorine-containing pyrazolecarbonitrile derivative according to claim 20, wherein, in compounds represented by Formulae (1), (3), (4), (5) and (6), Rf represents a difluoromethyl group, a chlorodifluoromethyl group, a pentafluoroethyl group, or a heptafluoropropyl group, R1 represents an alkyl group having 1 to 6 carbon atoms, and R3 and R4 respectively represent a methyl group.

23. A fluorine-containing pyrazolecarboxylic acid derivative represented by the following formula (2):

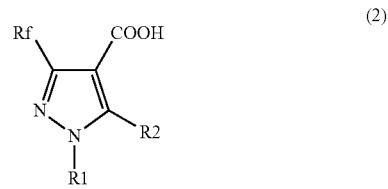

wherein, in Formula (2), Rf represents a perfluoroalkyl group having 2 to 6 carbon atoms; R1 represents an alkyl group having 1 to 6 carbon atoms; and R2 represents a hydrogen atom.

24. The fluorine-containing pyrazolecarboxylic acid derivative according to claim 23, wherein, in Formula (2), Rf represents a pentafluoroethyl group or a heptafluoropropyl group.

* * * * *